United States Patent
Pavlik et al.

(10) Patent No.: US 12,427,454 B2
(45) Date of Patent: Sep. 30, 2025

(54) FILTRATION SYSTEM AND METHOD FOR SYNCHRONIZING PERMEATE AND RETENTATE FLOW

(71) Applicant: Repligen Corporation, Waltham, MA (US)

(72) Inventors: Rudolf Pavlik, Huntington Beach, CA (US); Ralf Kuriyel, Waltham, MA (US)

(73) Assignee: Repligen Corporation, Waltham, MA (US)

( * ) Notice: Subject to any disclaimer, the term of this patent is extended or adjusted under 35 U.S.C. 154(b) by 60 days.

(21) Appl. No.: 17/852,643

(22) Filed: Jun. 29, 2022

(65) Prior Publication Data

US 2022/0331725 A1    Oct. 20, 2022

Related U.S. Application Data

(63) Continuation of application No. 17/721,846, filed on Apr. 15, 2022, now Pat. No. 11,673,083.
(Continued)

(51) Int. Cl.
  *B01D 35/26*   (2006.01)
  *B01D 29/11*   (2006.01)
  (Continued)

(52) U.S. Cl.
  CPC .............. *B01D 35/26* (2013.01); *B01D 29/11* (2013.01); *B01D 29/66* (2013.01); *B01D 29/902* (2013.01);
  (Continued)

(58) Field of Classification Search
  CPC ........ B01D 35/26; B01D 29/11; B01D 29/66; B01D 29/902; B01D 29/908; B01D 65/02;
  (Continued)

(56) References Cited

U.S. PATENT DOCUMENTS

| 4,986,918 A | 1/1991 | Breslau |
| 5,143,630 A | 9/1992 | Rolchigo |

(Continued)

FOREIGN PATENT DOCUMENTS

| AU | 2020401387 A1 | 6/2022 |
| CN | 201728062 U | 2/2011 |

(Continued)

OTHER PUBLICATIONS

International Search Report and Written Opinion for the International Patent Application No. PCT/US22/24960, mailed Aug. 19, 2022, 14 pages.
(Continued)

*Primary Examiner* — Hayden Brewster
(74) *Attorney, Agent, or Firm* — KDW Firm PLLC

(57) ABSTRACT

A fluid filtration system includes a fluid storage vessel such as a bioreactor, a filter housing including a filter element disposed therein, a pump coupled between the fluid storage vessel and the filter housing, and a flow diverter disposed between the pump and the filter housing. The pump is configured to move fluid from the fluid storage vessel through the filter element, and the flow diverter is configured for selectively directing fluid received from the pump to the first or second end of the filter housing. In a first mode of operation, the flow diverter directs flow through the filter housing in a first direction, while in a second mode of operation, the flow diverter directs flow through the filter housing in a second direction opposite the first direction.

20 Claims, 16 Drawing Sheets

Related U.S. Application Data

(60) Provisional application No. 63/176,134, filed on Apr. 16, 2021.

(51) Int. Cl.
| | |
|---|---|
| *B01D 29/66* | (2006.01) |
| *B01D 29/90* | (2006.01) |
| *B01D 65/02* | (2006.01) |
| *B01D 69/08* | (2006.01) |
| *C12M 1/00* | (2006.01) |
| *C12M 1/34* | (2006.01) |

(52) U.S. Cl.
CPC .......... *B01D 29/908* (2013.01); *B01D 65/02* (2013.01); *B01D 69/08* (2013.01); *C12M 29/16* (2013.01); *C12M 41/44* (2013.01); *B01D 2201/165* (2013.01); *B01D 2321/04* (2013.01); *B01D 2321/12* (2013.01)

(58) Field of Classification Search
CPC .......... B01D 69/08; B01D 2201/165; B01D 2321/04; B01D 2321/12; C12M 29/16; C12M 41/44
See application file for complete search history.

(56) References Cited

U.S. PATENT DOCUMENTS

| | | | |
|---|---|---|---|
| 5,383,491 | A | 1/1995 | Heilman |
| 5,466,384 | A | 11/1995 | Prevost et al. |
| 6,060,306 | A | 5/2000 | Flatt |
| 6,079,691 | A | 6/2000 | Dragone |
| 6,165,355 | A | 12/2000 | Coulonvaux et al. |
| 6,248,809 | B1 | 6/2001 | Buckley |
| 6,755,970 | B1 | 6/2004 | Knappe |
| 7,875,448 | B2 | 1/2011 | Furey |
| 8,794,263 | B2 | 8/2014 | Scott et al. |
| 9,375,683 | B2 | 6/2016 | Becker et al. |
| 9,663,753 | B2 | 5/2017 | Gebauer |
| 9,895,635 | B2 | 2/2018 | Levitt |
| 10,286,338 | B2 | 5/2019 | Levitt |
| 11,110,398 | B2 | 9/2021 | Nutalapati et al. |
| 2001/0000895 | A1 | 5/2001 | Ilias |
| 2005/0158851 | A1 | 7/2005 | Furey |
| 2008/0179244 | A1 | 7/2008 | Morgan et al. |
| 2008/0296237 | A1 | 12/2008 | Hammond |
| 2009/0090661 | A1 | 4/2009 | Tanner |
| 2011/0024353 | A1* | 2/2011 | Jonsson .............. A61M 60/435 210/139 |
| 2014/0014581 | A1 | 1/2014 | Chancellor |
| 2014/0079143 | A1 | 3/2014 | Canton |
| 2014/0097143 | A1 | 4/2014 | Clements et al. |
| 2014/0299532 | A1* | 10/2014 | Becker ................ B01D 63/107 210/321.69 |
| 2015/0158907 | A1 | 6/2015 | Zhou et al. |
| 2019/0083903 | A1 | 3/2019 | Chan et al. |
| 2019/0241856 | A1 | 8/2019 | Wales et al. |
| 2019/0338238 | A1 | 11/2019 | Lu et al. |
| 2019/0381458 | A1 | 12/2019 | De Los Reyes et al. |
| 2020/0392449 | A1 | 12/2020 | Griffin et al. |
| 2021/0030943 | A1 | 2/2021 | Gao |
| 2021/0039045 | A1* | 2/2021 | Perreault ............. B01D 61/146 |
| 2021/0261900 | A1 | 8/2021 | Bhargav et al. |
| 2021/0395664 | A1 | 12/2021 | Paul et al. |
| 2022/0184558 | A1 | 6/2022 | Popova et al. |

FOREIGN PATENT DOCUMENTS

| | | |
|---|---|---|
| CN | 107355566 A | 11/2017 |
| CN | 209818796 U | 12/2019 |
| EP | 3419741 A2 | 1/2019 |
| EP | 2257363 B2 | 2/2019 |
| EP | 3950921 A1 | 2/2022 |
| EP | 4013845 A1 | 6/2022 |
| GB | 2581844 A | 9/2020 |
| JP | S5263876 A | 5/1977 |
| WO | 2005042768 A2 | 5/2005 |
| WO | 2017029305 A1 | 2/2017 |
| WO | 2020043550 A1 | 3/2020 |
| WO | 2021119600 A1 | 6/2021 |
| WO | 2022132732 A1 | 6/2022 |

OTHER PUBLICATIONS

Supplementary Partial European Search Report and Provisional Opinion Accompanying the Partial Search Result issued in EP Application 22788986.2, dated Sep. 10, 2024, 17 pages.
The International Search Report and Written Opinion mailed Mar. 25, 2024, for the Application No. PCT/US2023/076344 (28 pages).

* cited by examiner

FILTRATION SYSTEM AND METHOD FOR SYNCHRONIZING PERMEATE AND RETENTATE FLOW

CROSS-REFERENCE TO RELATED APPLICATIONS

This application is a continuation of U.S. nonprovisional patent application Ser. No. 17/721,846 filed Apr. 15, 2022, which claims the benefit of and priority under 35 U.S.C. § 119 to U.S. provisional patent application Ser. No. 63/176,134 filed Apr. 16, 2021, the entirety of which applications are incorporated by reference herein for all purposes.

BACKGROUND OF THE DISCLOSURE

Field of the Disclosure

Embodiments of the disclosure relate generally to filtration systems, and more particularly to a filtration system including a single pump for selectively providing flow in two opposing directions through a filter member.

Discussion of Related Art

Filtration is often performed to separate, clarify, modify, and/or concentrate a fluid solution, mixture, or suspension. In the biotechnology, pharmaceutical, and medical industries, filtration is vital for the successful production, processing, and analysis of drugs, diagnostics, and chemicals as well as many other products. As examples, filtration may be used to sterilize fluids and to clarify a complex suspension into a filtered "clear" fraction and an unfiltered fraction. Similarly, constituents in a suspension may be concentrated by removing or "filtering out" the suspending medium. Further, with appropriate selection of filter material, filter pore size and/or other filter variables, many other specialized uses have been developed. These uses may involve selective isolation of constituents from various sources, including cultures of microorganisms, blood, as well as other fluids that may be solutions, mixtures, or suspensions.

Biologics manufacturing processes have advanced through substantial process intensification. Both eukaryotic and microbial cell culture to produce recombinant proteins, virus-like particles (VLP), gene therapy particles, and vaccines now include cell growth techniques that can achieve 100e6 cells/ml or higher. This is achieved using cell retention devices that remove metabolic waste products and refresh the culture with additional nutrients. One common means of cell retention is to perfuse a bioreactor culture using hollow fiber filtration using alternating tangential flow (ATF).

Commercial and development scale processes use a device that controls a pump to perform ATF through a hollow fiber filter. Typically, these systems are arranged so that the pump moves fluid through the filter in a single direction. This results in the culture spending an undesirably long time outside the bioreactor and can also cause premature fouling of the hollow fiber filter.

It would be desirable, therefore, to provide an improved pumping arrangement that increases the utilization of the entire filter length of a hollow fiber filter used in connection with a vessel such as a bioreactor vessel. It would also be desirable to provide a pumping arrangement that enhances the overall efficiency of the pumping system.

SUMMARY OF THE DISCLOSURE

A fluid filtration system can include a fluid storage vessel, a filter housing including a filter element disposed therein, the filter housing having first and second ends, a pump coupled between the fluid storage vessel and the filter housing, and a flow diverter disposed between the pump and the filter housing. The pump is configured to move fluid from the fluid storage vessel through the filter element. The flow diverter is configured for selectively directing fluid received from the pump to the first or second end of the filter housing.

The system further includes a first filtration line coupled between the first end of the filter housing and a first outlet of the flow diverter, a first return line disposed between the fluid storage vessel and the first filtration line, and a first isolation valve disposed in the first return line to selectively permit fluid flow between the filter housing and the fluid storage vessel via the first return line. The system further includes a second filtration line coupled between the second end of the filter housing and a second outlet port of the three-way valve, a second return line disposed between the fluid storage vessel and the second filtration line, and a second isolation valve disposed in the second return line to selectively permit fluid flow between the filter housing and the fluid storage vessel through the second return line.

The system can include a flow sensor for determining actual flowrate from a discharge portion of the pump. The system can include a controller coupled to the pump, the flow sensor, the first and second isolation valves and the flow diverter to selectively control a fluid flow path through the system. The system can include memory associated with the controller, the memory storing a plurality of preset positions of the first and second isolation valves and the flow diverter. The controller may adjust a speed of the pump based on sensed flowrate information received from the flow sensor.

In some embodiments the pump is a low shear pump. In some embodiments the filter element is a hollow fiber filter. In some embodiments the fluid storage vessel is a bioreactor. In some embodiments the fluid comprises cell cultures. The cell culture can be a fed-batch cell culture or a concentrated fed-batch cell culture, and the disclosed systems and methods can be used to produce any of a variety of desired cell products including but not limited to endogenous and recombinant products, including proteins, peptides, nucleic acids, virus, amino acids, antibiotics, specialty chemicals and other molecules of value. Desired proteins may include but are not limited to monoclonal antibodies, enzymes and other recombinant antibodies, enzymes, peptides, virus.

In some embodiments the flow diverter comprises a three-way valve. In other embodiments the flow diverter comprises first and second flow diverter isolation valves, the first flow diverter isolation valve disposed between the pump discharge line and the first filtration line, and the second flow diverter isolation valve disposed between the pump discharge line and the second filtration line.

A method of operating a fluid filtration system to provide two-directional flow through a filter housing is disclosed. The method can include: in a first mode of operation, transferring fluid from a fluid storage vessel to a first end of the filter housing by configuring a flow diverter to direct flow of said fluid from a pump through a first filtration line coupled to the first end of the filter housing; and in a second mode of operation, transferring said fluid from said fluid storage vessel to a second end of the filter housing by configuring the flow diverter to direct flow of said fluid from said pump through a second filtration line coupled to the second end of the filter housing. In the first mode of operation fluid travels from the first end of the filter housing to the second end of the filter housing, and in the second mode of operation fluid travels from the second end of the filter housing to the first end of the filter housing.

The method may further include, in the first mode of operation, directing the flow of fluid from the second end of the filter housing to the fluid storage vessel via a first return line, and in the second mode of operation, directing said flow of fluid from the first end of the filter housing to the fluid storage vessel via a second return line.

The method may further include, in the first mode of operation, the step of directing said flow of said fluid from the second end of the filter housing to the fluid storage vessel comprises opening an isolation valve disposed in the first return line and closing an isolation valve disposed in the second return line. The method may further include, in the second mode of operation, the step of directing said flow of said fluid from the first end of the filter housing to the fluid storage vessel comprises opening an isolation valve disposed in the second return line and closing an isolation valve disposed in the first return line. The method may further include adjusting a speed of said pump based on an output of a flow sensor disposed downstream of the pump.

In some embodiments the pump is a low shear pump. In some embodiments the filter element is a hollow fiber filter. In some embodiments the fluid storage vessel is a bioreactor. In some embodiments the fluid comprises cell cultures.

In some embodiments the flow diverter comprises a three-way valve. In other embodiments the flow diverter comprises first and second flow diverter isolation valves, the first flow diverter isolation valve disposed between the pump and the first filtration line, and the second flow diverter isolation valve disposed between the pump and the second filtration line.

A valve is disclosed for diverting flow received from a pump. The valve can include a base portion, first and second side supports coupled to the base portion, first and second stationary plates fixedly coupled to the first and second side supports, first and second movable plates movably coupled to the first and second side supports, and an actuating member coupled to the first and second movable plates to selectively move the first and second movable plates toward, and away from, the first and second stationary plates. The first movable plate can be disposed between the first and second stationary plates, and the second movable plate can be disposed between the second stationary plate and the base portion. First and second flexible tubes are positionable between the base portion and the second movable plate, and third and fourth flexible tubes are positionable between the first movable plate and the first stationary plate.

In a first position of the valve the second movable plate is offset from the base portion by a distance equal to or greater than the outside diameter of the first and second flexible tubes to allow fluid to flow through the first and second flexible tubes. In the first position the first movable plate is offset from the first stationary plate by an amount sufficient to compress the third and fourth flexible tubes to prevent fluid from flowing through the third and fourth flexible tubes.

In a second position of the valve the second movable plate is offset from the base portion by an amount sufficient to compress the first and second flexible tubes to prevent fluid from flowing through the first and second flexible tubes. In the second position the first movable plate is offset from the first stationary plate by a distance equal to or greater than the outside diameter of the third and fourth flexible tubes to allow fluid to flow through the third and fourth flexible tubes.

In some embodiments the actuating member is coupled to an actuator, the actuator controllable by a controller coupled thereto.

BRIEF DESCRIPTION OF THE DRAWINGS

The accompanying drawings illustrate preferred embodiments of the disclosed method so far devised for the practical application of the principles thereof, and in which.

DESCRIPTION OF EMBODIMENTS

A system is disclosed, comprising a bioreactor, a pump and a filter. The pump moves fluid in alternating directions through the filter via associated piping and a flow diverter such as, but not limited to, a three-way valve, a rotary valve, a pinch valve, or a shuttle valve. The system can be employed for conducting a rapid, low sheer, Alternating Tangential Flow (ATF) of fluid through the filter, which in some embodiments is a hollow fiber filter. Such a system has applications in perfusion of cultured animal cells as well as other varied filtration applications.

As will be discussed in greater detail later, the disclosed assembly can reduce the amount of time cell cultures reside outside the bioreactor and can also provide a more uniform use of the filter as well as reduced fouling, compared to current systems. In some embodiments, operational control of the pump can be based on an algorithm which can periodically apply an operational subroutine that facilitates a filter cleaning/backflush function. These and other advantage will be discussed below.

Figure 1:
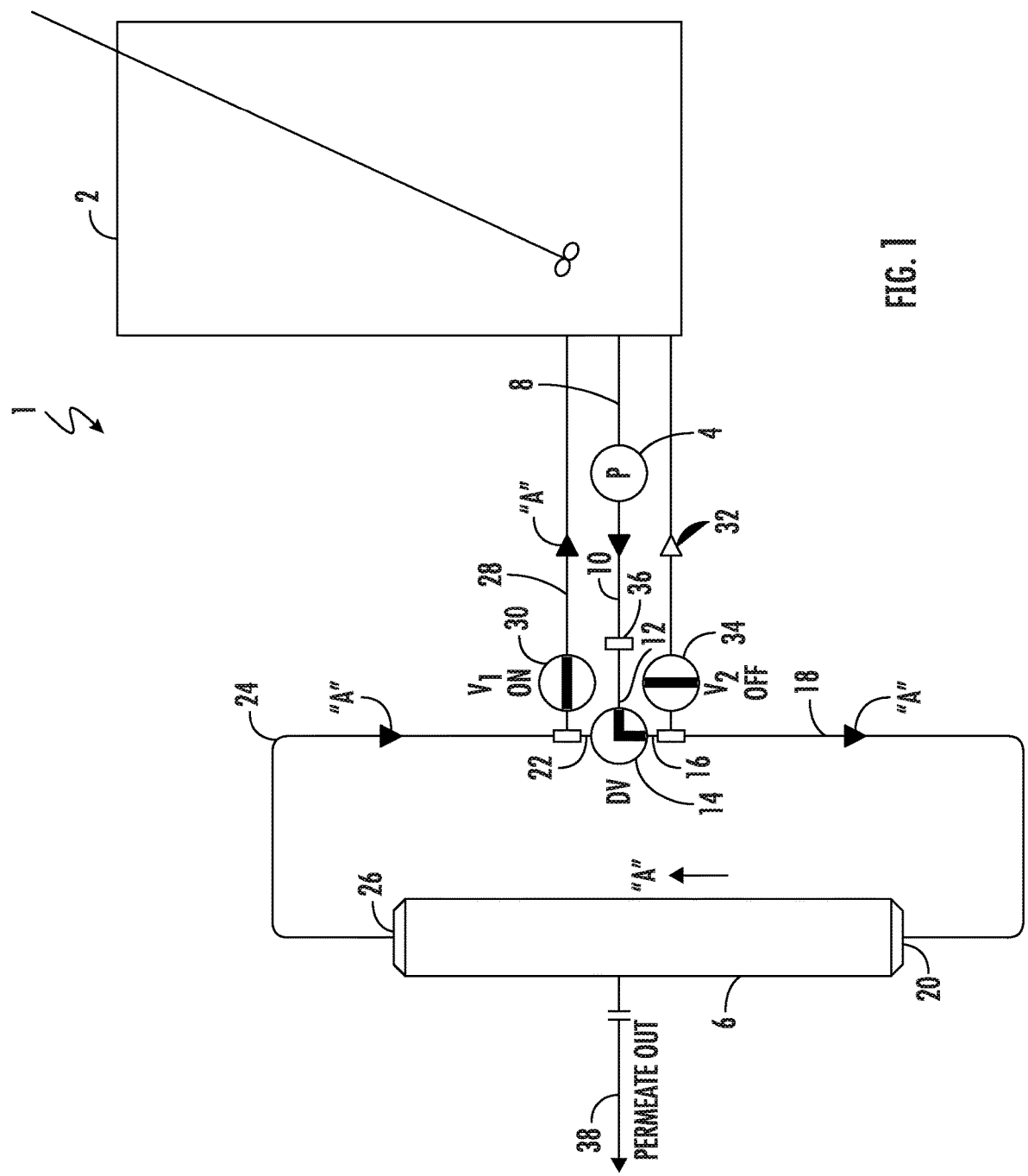
FIG. 1 is a schematic view of an example pump and filter system according to the present disclosure operating in a first flow mode.
Figure 2:
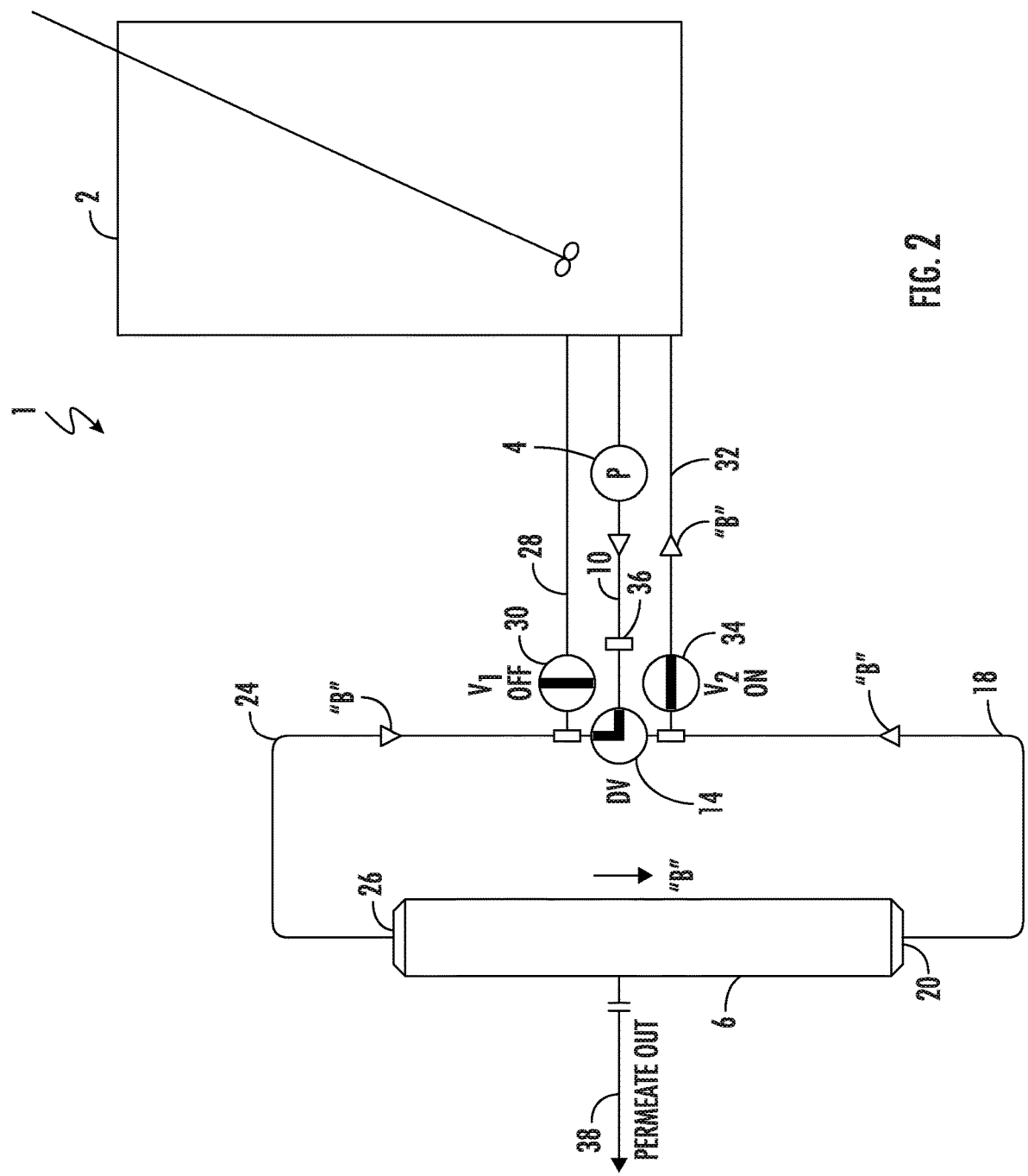
FIG. 2 is a schematic view of the example pump and filter system of FIG. 1 operating in a second flow mode.

FIGS. 1 and 2 illustrate an example system 1 which can include a fluid storage vessel 2 (referred to herein as "vessel") coupled to a pump 4 and a filter housing 6. The pump 4 is arranged to take suction from the vessel 2 via a suction line 8 disposed at or near the bottom of the vessel 2. The pump 4 is coupled to a discharge line 10, which in turn is coupled to an inlet port 12 of a flow diverter, which in the illustrated embodiment is a three-way valve 14. A first outlet port 16 of the three-way valve 14 is coupled to a first filtration line 18, which in turn is coupled to a first end 20 of the filter housing 6. A second outlet port 22 of the three-way valve 14 is coupled to a second filtration line 24, which in turn is coupled to a second end 26 of the filter housing 6. A first return line 28 is coupled between the second filtration line 24 and the vessel 2. A first isolation valve 30 is disposed in the first return line 28 for selectively enabling flow between the vessel 2 and the second end 26 of the filter housing 6. A second return line 32 is coupled between the first filtration line 18 and the vessel 2. A second isolation valve 34 is disposed in the second return line 32 for selectively enabling flow between the vessel 2 and the first end 20 of the filter housing 6. In some embodiments a flow switch 36 may be disposed in the discharge line 10 between the pump 4 and the three-way valve 14.

It will be appreciated that it in some embodiments it is desirable to minimize the length of the discharge and return lines between the vessel 2 and the filter housing 6 in order to minimize cell culture exposure out of the vessel.

The filter housing 6 encloses a filter element (not shown), which in one non-limiting exemplary embodiment is a hollow fiber filter, although this is not critical and any of a variety of other filter elements can be used. The filter housing 6 can be made from plastic, metal, such as stainless steel, glass, and the like. Suitable filter elements include hollow fiber filters, screen filters, and the like. In one non-limiting example embodiment, the filter element is a hollow fiber filter (see, e.g., FIG. 13). In some implementations, the hollow fiber filter has a pore size of about 0.1 to 5.0 microns, e.g., 0.2, 0.3, 0.4, 0.5, 0.6, 0.7, 0.8, or 0.9 microns, or 1, 2, 3, or 4 microns, or about 500 to 1000 kD, e.g., 550, 600, 650, 700, 750, 800, 850, 900, or 950 kD.

To minimize the negative impact of pumping on the cells within the pumped fluid, a specialized pump type is desirable. In the illustrated embodiment the pump 4 is a diaphragm pump, however, it will be appreciated that the disclosure is not so limited, and thus the pump 4 can be any appropriate low-shear pump type, examples of which include Levitronix pumps (www.levitronix.com), and Quattroflow pumps manufactured by Holland Applied Technologies (www.hollandapt.com). Peristaltic pumps can be used for non-cell culture applications. Moreover, permeate and retentate pumps can be peristaltic pumps.

The vessel 2 may be any suitable container for housing a fluid to be filtered. For example, the fluid vessel may be a bioreactor, a fermentor or any other vessel, nonexclusively including vats, barrels, tanks, bottles, flasks, containers, and the like which can contain liquids. The vessel may be composed of any suitable material such as plastic, metal such as stainless steel, glass, or the like.

In general, the pump 4, three-way valve 14, and first and second isolation valves 30, 32 function to selectively provide flow from the vessel 2 through the filter housing 6 (and filter element therein) in one or two different directions.

In a first mode of operation, illustrated in FIG. 1, the system 1 is configured to direct flow from the vessel 2 to the first end 20 of the filter housing 6 via first filtration line 18. Thus, the three-way valve 14 is operated to direct flow from the pump 4 to the first filtration line 18. The second isolation valve 34 is operated to assume the "closed" position thus preventing flow between the first filtration line 18 and the second return line 32. Fluid thus flows from the vessel 2, through the pump 4, through the three-way valve 14, through the first filtration line 18 where it enters the first end 20 of the filter housing 6. Fluid travels through the filter housing 6 in the direction of arrow "A" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, the first isolation valve 30 (operated to assume the "open" position), and the first return line 28.

In a second mode of operation, illustrated in FIG. 2, the system 1 is configured to direct flow from the vessel 2 to the second end 26 of the filter housing 6 via second filtration line 24. Thus, the three-way valve 14 is operated to direct flow from the pump 4 to the second filtration line 24. The first isolation valve 30 is operated to assume the "closed" position thus preventing flow between the second filtration line 24 and the first return line 28. Fluid thus flows from the vessel 2, through the pump 4, through the three-way valve 14, through the second filtration line 24 where it enters the second end 26 of the filter housing 6. Fluid travels through the filter housing 6 in the direction of arrow "B" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 32, the second isolation valve 30 (operated to assume the "open" position), and the second return line 32.

With the disclosed system 1, a single pump 4 can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode.

In an alternating tangential flow mode, cell culture flow is re-directed by the three-way valve 14 with a simultaneous opening and closing of the first and second isolation valves 30, 34. In addition, where the system 1 is configured to accommodate alternating tangential flow, the pump 4 may not displace the entire volume of cell culture from the vessel 2. Rather, multiple pump cycles may be required in order to move the entire volume of cell culture through the filter housing 6. Time based pumping commanded by flow of the proposed technology guaranies full exchange of cell culture in one recirculation loop cycle.

The time of flow one direction is the time when a single particulate (cell) travels from the vessel 2 (e.g., bioreactor) through the entire loop of piping (tubing), through the filter 6, and returns to the vessel. This time depends on the flow rate set by the pump 4. An algorithm performed by the controller 44 (see FIG. 10) calculates the time required for the cells to make the complete loop. The same time is than applied to flow of cells the opposite direction. When the pump 4 is set to run at a low flowrate, it will take relatively longer for the cells to make a complete loop in one direction, while setting the pump to run at a higher flowrate will result in a shorter time for the cells to make a complete loop in one direction. The disclosed alternating flow arrangement (i.e., flow through the loop in a first direction follow by flow through the loop in a second, opposite, direction), can be effective in preventing premature filter clogging. Flow through the permeate discharge line 38 can be adjusted by adjusting the speed of the associated permeate pump (not shown) and may be based on the flow rate of a retentate pump (not shown). Retentate and permeate pump flow rate can be periodically increased for a short time period to further help with the cleaning of the filter and to increase its life.

Figure 3:
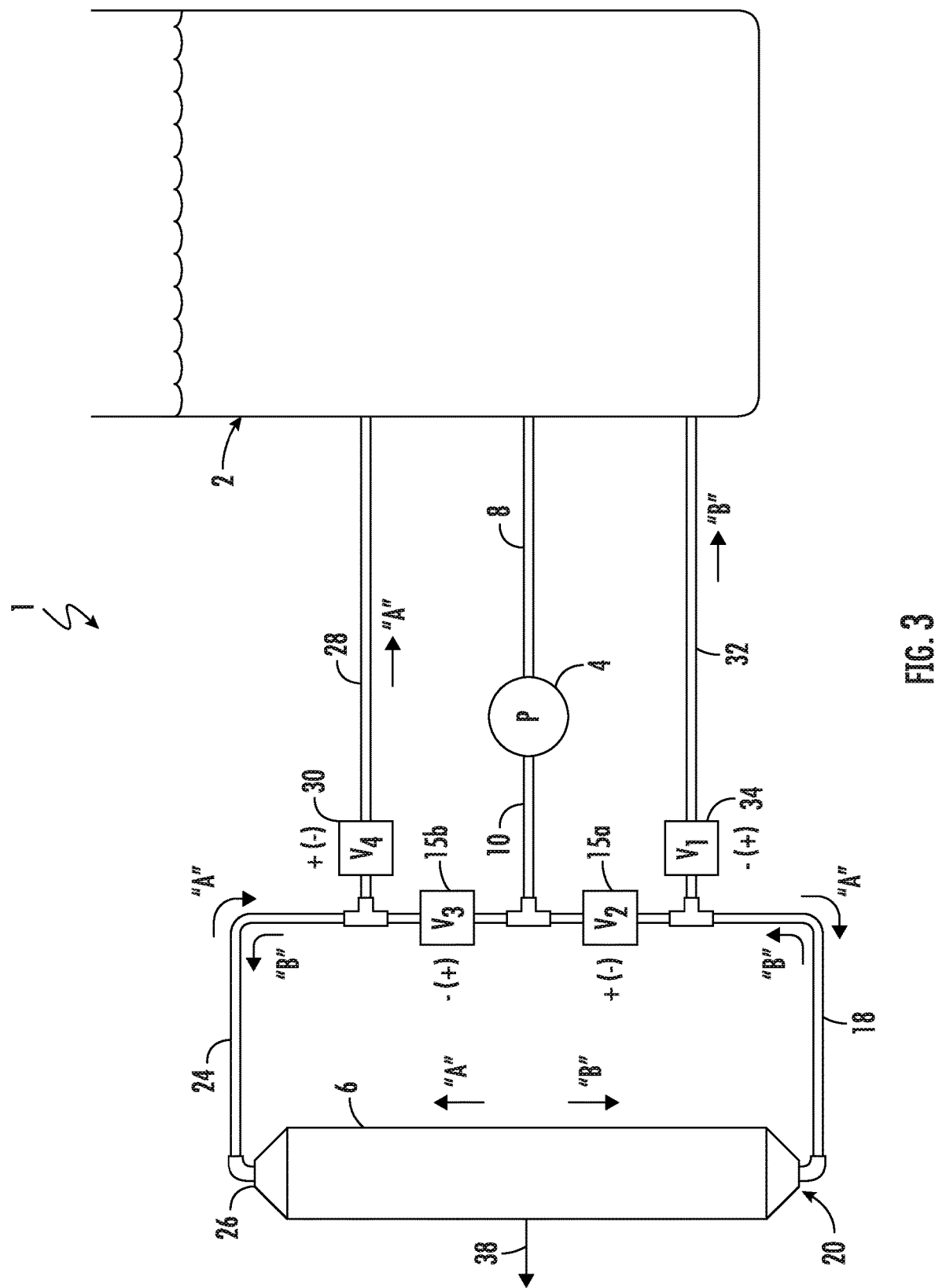
FIG. 3 is a schematic view of another example pump and filter system according to the present disclosure.

FIG. 3 illustrates an alternative embodiment of the disclosed system 1 in which the flow diverter comprises first and second flow diverter isolation valves 15A, 15B. As can be seen, the system 1 of FIG. 3 is substantially the same as the system described in relation to FIGS. 1 and 2, including vessel 2, pump 4, and filter housing 6, along with pump suction and discharge lines 8, 10, first and second filtration lines 18, 24, first and second return lines 28, 32 and first and second isolation valves 30 and 34, all of which function in the same matter described in relation to FIGS. 1 and 2. The first flow diverter isolation valve 15A is disposed between the pump discharge line 10 and the first filtration line 18. The second flow diverter isolation valve 15B is disposed between the pump discharge line 10 and the second filtration line 24. As will be appreciated, the operation of the first and second flow diverter isolation valves 15A, B, taken together, can function to divert flow in the same manner as described for the three-way valve 14 of the previous embodiments.

Thus, to effect flow through the filter housing 6 (and filter) in the direction of arrow "A" (i.e., the first mode of operation, in which the system 1 is configured to direct flow from the vessel 2 to the first end 20 of the filter housing 6 via first filtration line 18), the first flow diverter isolation valve 15a is configured in the open position while the second flow diverter isolation valve 15b is configured in the closed position. Thus configured, flow from the pump 4 is directed to the first filtration line 18. The second isolation valve 34 is operated to assume the "closed" position thus preventing flow between the first filtration line 18 and the second return line 32. Fluid thus flows from the vessel 2, through the pump 4, through the first flow diverter isolation valve 15a, and through the first filtration line 18 where it enters the first end 20 of the filter housing 6. Fluid travels through the filter housing 6 in the direction of arrow "A" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, the first isolation valve 30 (operated to assume the "open" position), and the first return line 28.

To effect flow through the filter housing 6 (and filter) in the direction of arrow "B" (i.e., the second mode of operation, in which the system 1 is configured to direct flow from the vessel 2 to the second end 26 of the filter housing 6 via second filtration line 24), the first flow diverter isolation valve 15A is configured in the closed position while the second flow diverter isolation valve 15B is configured in the open position. Thus configured, flow from the pump 4 is directed to the second filtration line 24. The first isolation valve 30 is operated to assume the "closed" position thus preventing flow between the second filtration line 24 and the first return line 28. Fluid thus flows from the vessel 2, through the pump 4, through the second flow diverter isolation valve 15b, and through the second filtration line 24 where it enters the second end 26 of the filter housing 6. Fluid travels through the filter housing 6 in the direction of arrow "B" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the first filtration line 18, the second isolation valve 30 (operated to assume the "open" position), and the second return line 32.

With the embodiment of FIG. 3, a single pump 4 can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode.

Figure 4A:
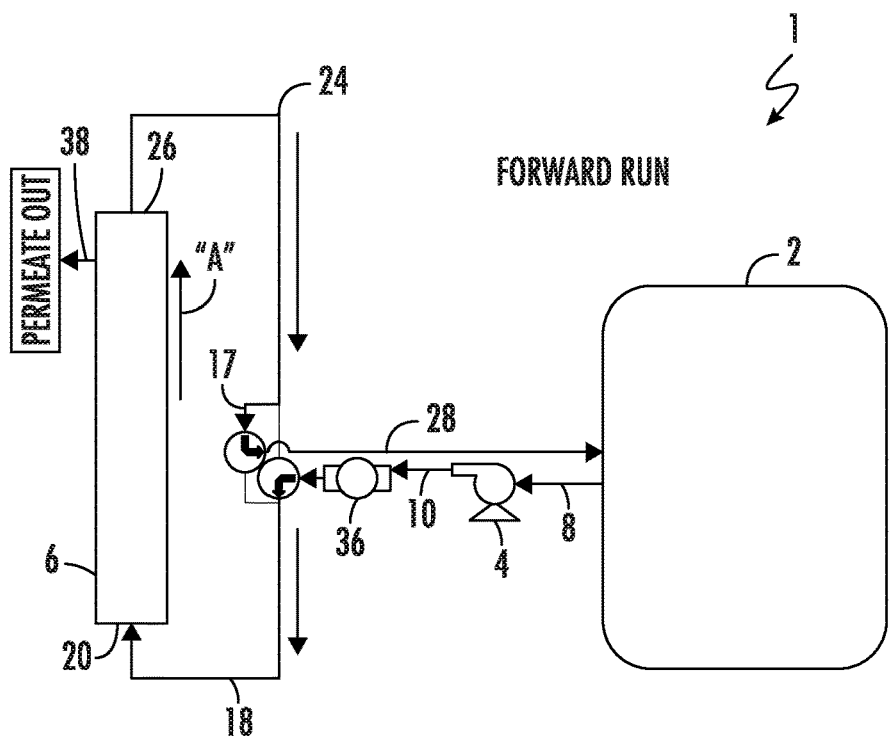
FIGS. 4A and 4B are schematic views of another example pump and filter system according to the present disclosure.
Figure 4B:
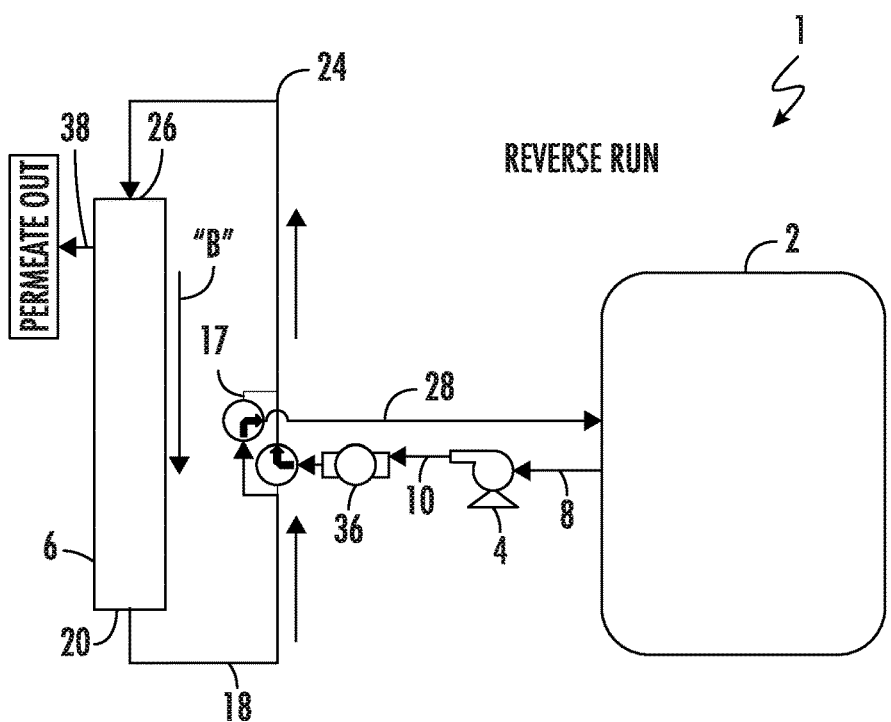
Figure 5:
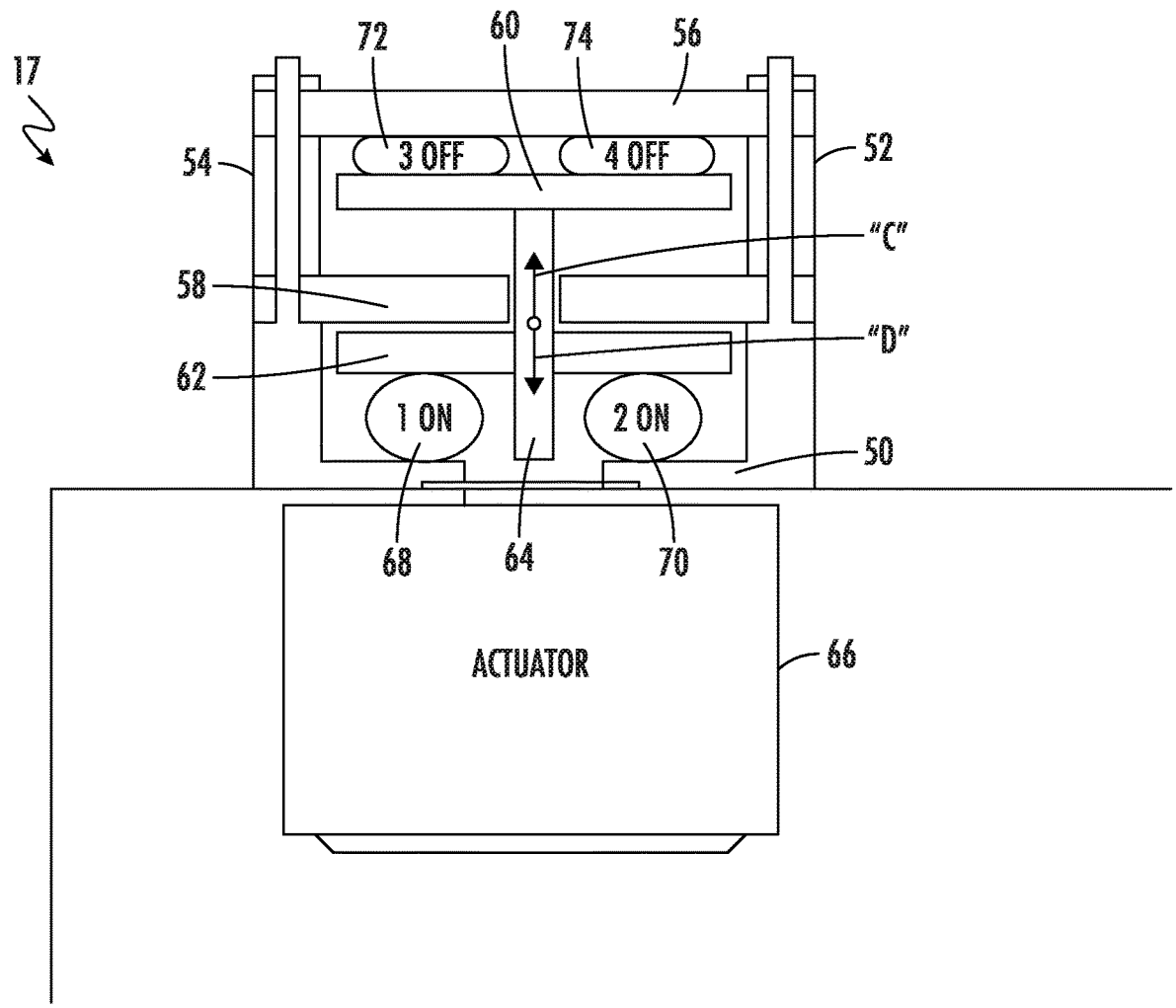
FIG. 5 is a schematic view of an example valve according to the present disclosure.

FIGS. 4A and 4B illustrate an alternative embodiment of the disclosed system 1 in which the flow diverter comprises a pinch valve 17 (FIG. 5). As can be seen, the system 1 of FIGS. 4A and 4B is substantially the same as the system described in relation to FIGS. 1 and 2, including vessel 2, pump 4, and filter housing 6, along with pump suction and discharge lines 8, 10, first and second filtration lines 18, 24, and first return line 28. The system 1 of FIGS. 4A and 4B notably does not include a second return line nor does it include the first and second isolation valves 30 and 34. The pinch valve 17 is disposed between the pump discharge line 10 and the first and second filtration lines 18, 28. As arranged, the operation of the pinch valve 17 functions to divert flow in the same manner as described for the three-way valve 14 of FIG. 1.

To effect flow through the filter housing 6 (and filter) in the direction of arrow "A" (i.e., the first mode of operation, illustrated in FIG. 4A, in which the system 1 is configured to direct flow from the vessel 2 to the first end 20 of the filter housing 6 via first filtration line 18), the pinch valve 17 is configured to direct flow from the pump discharge 10 to the first filtration line 18, and to block flow from the pump discharge to the second filtration line 24. In this configuration, the pinch valve 17 is also configured to direct flow from the second filtration line 24 to the first return line 28. Thus configured, fluid flows from the vessel 2, through the pump 4, through the pinch valve 17, then through the first filtration line 18 where it enters the first end 20 of the filter housing 6. Fluid travels through the filter housing 6 in the direction of arrow "A" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, pinch valve 17, and first return line 28.

To effect flow through the filter housing 6 (and filter) in the direction of arrow "B" (i.e., the second mode of operation, shown in FIG. 4B, in which the system 1 is configured to direct flow from the vessel 2 to the second end 26 of the filter housing 6 via second filtration line 24), is configured to direct flow from the pump discharge 10 to the second filtration line 18, and to block flow from the pump discharge 10 to the first filtration line 18. In this configuration, the pinch valve 17 is also configured to direct flow from the first filtration line 24 to the first return line 28. Thus configured, fluid flows from the vessel 2, through the pump 4, through the pinch valve 17, then through the second filtration line 24 where it enters the second end 26 of the filter housing 6. Fluid travels through the filter housing 6 in the direction of arrow "B" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the first filtration line 18, pinch valve 17, and first return line 28.

With the embodiment of FIGS. 4A and 4B, a single pump 4 can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode.

FIG. 5 illustrates an example pinch valve 17 for use in the example system of FIGS. 4A and 4B. The pinch valve 17 comprises a base portion 50, first and second side supports 52, 54, first and second stationary plates 56, 58 and first and second movable plates 60, 62. The base portion 50 can have an opening (not shown) to receive an actuating member 64 of an actuator 66 therethrough. The actuating member 64 may be coupled to the first and second movable plates 60, 62 to adjust the positions of the first and second movable plates with respect to the base portion 50 and the first and second stationary plates 56, 58. As will be described in greater detail, when a plurality of flexible tubes are disposed between the first and second movable plates 60, 62 and the first and second stationary plates 56, 58, fluid flow can be selectively controlled through the flexible tubes by compressing or pinching selected ones of the flexible tubes so that fluid cannot flow therethrough. Allowing fluid to flow through the remaining uncompressed tubes enables flow between selected components of the system 1 to be controlled.

The first and second stationary plates 56, 58 may be fixed to the base portion 50 via the first and second side supports 52, 54 so they do not move during operation of the pinch valve 17. The first and second movable plates 60, 62 are slidable along the first and second side supports 52 so they can reciprocate during operation of the pinch valve 17. The actuating member 64 is coupled to the first and second movable plates 60, 62 so the actuator 66 may selectively reciprocate the first and second movable plates between first and second positions. In the first position (shown in FIG. 5), the actuating member is moved in the direction of arrow "C" so that the first movable plate 60 is moved toward the first stationary plate 56, and the second movable plate 62 is moved toward the second stationary plate 58. In the second position (not shown), the actuating member is moved in the direction of arrow "D" so that the first movable plate 60 is moved toward the second stationary plate 58, and the second movable plate 62 is moved toward the base portion 50.

A plurality of flexible tubes can be disposed between the first and second stationary plates 56, 58 and the first and second movable plates 60, 62. In the illustrated embodiment, first and second flexible tubes 68, 70 are disposed between the base portion 50 and the second movable plate 62, while third and fourth flexible tubes 72, 74 are disposed between the first movable plate 60 and the first stationary plate 56. The flexible tubes may be made from any material appropriate for bioprocessing applications, such as fluoropolymer or the like.

As can be seen, when the pinch valve 17 is moved to the first position shown in FIG. 5, (i.e., the actuating member 64 and the first and second movable plates 60, 62 are moved in the direction of arrow "C"), the second movable plate 62 moves away from the base portion 50 by a sufficient distance (e.g., an amount equal to or greater than the outside diameter of the first and second flexible tubes 68, 70) that the first and second flexible tubes 68, 70 are substantially uncompressed, thus allowing fluid to flow through the first and second flexible tubes. By contrast, in the first position the first movable plate 60 moves toward the first stationary plate by an amount sufficient to compress the third and fourth flexible tubes 72, 74, and prevent fluid from flowing through the third and fourth flexible tubes.

When the pinch valve 17 is moved to the second position (i.e., the actuating member 64 and the first and second movable plates 60, 62 are moved in the direction of arrow "D"), the second movable plate 62 moves toward the base portion 50 by an amount sufficient to compresses the first and second flexible tubes 68, 70 and prevent fluid from flowing through the first and second flexible tubes. By contrast, in the second position the first movable plate 60 moves away from the first stationary plate 56 by a sufficient distance (e.g., an amount equal to or greater than the outside diameter of the third and fourth flexible tubes 72, 74) so that the third and fourth flexible tubes are substantially uncompressed, thus allowing fluid to flow through the third and fourth flexible tubes.

When the pinch valve 17 is integrated into the system 1 shown in FIGS. 4A and 4B, the first flexible tube 68 may be coupled between the second filtration line 24 and the first return line 28, the second flexible tube 70 may be coupled between the pump discharge 10 and the first filtration line 18, the third flexible tube 72 may be coupled between 10 and 24, and the fourth flexible tube 74 may be coupled between the first filtration line 18 and 28. Thus arranged, in the first position of the pinch valve 17 (i.e., the position shown in FIG. 5), the first and second flexible tubes 68, 70 are uncompressed and flow is enabled between the second filtration line 24 and the first return line 28, and between the pump discharge 10 and the first filtration line 18. The third and fourth flexible tubes 72, 74 are compressed, and flow is prevented between the pump discharge 10 and the second filtration line 24, and between the first filtration line 18 and the first return line 28. Thus, in the first position of the pinch valve 17 flow from the bioreactor 2 enters the first end 20 of the filter 6 and returns to the bioreactor via the first return line 28.

To reverse flow through the filter 6, the pinch valve 17 is moved to the second position so that the first and second flexible tubes 68, 70 are compressed so that flow is prevented between the second filtration line 24 and the first return line 28, and between the pump discharge 10 and the first filtration line 18, while the third and fourth flexible tubes 72, 74 are uncompressed and flow is enabled between the first filtration line 18 and the first return line 28, and between the pump discharge 10 and the second filtration line 24. Thus, in the second position of the pinch valve 17 flow from the bioreactor 2 enters the first end 20 of the filter 6 and returns to the bioreactor via the first return line 28.

An advantage to the use of pinch valve 17 in the system 1 of FIGS. 4A and 4B is that it eliminates liquid contact with internal valve components and offers instant flow redirection (limited only by the time it takes to move the actuating member 64 between the first and second positions).

Figure 6A:
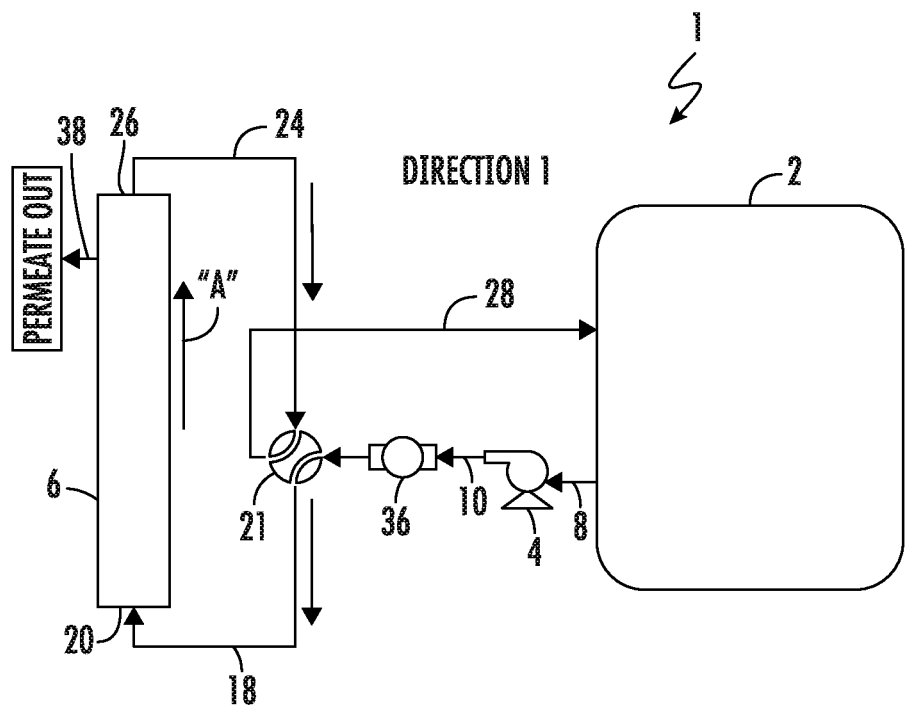
FIGS. 6A and 6B are schematic views of another example pump and filter system according to the present disclosure.
Figure 6B:
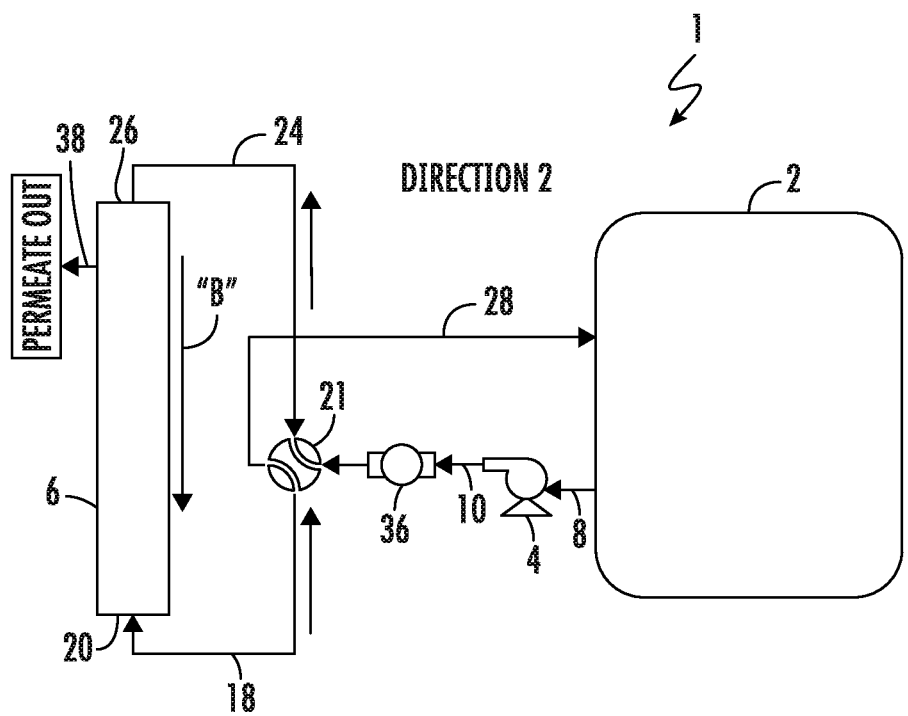

FIGS. 6A and 6B illustrate an alternative embodiment of the disclosed system 1 in which the flow diverter is a rotary valve 21. As can be seen, the system 1 of 6A and 6B is substantially the same as the system described in relation to FIGS. 1 and 2, including vessel 2, pump 4, and filter housing 6, along with pump suction and discharge lines 8, 10, first and second filtration lines 18, 24, and first return line 28. The system 1 of FIGS. 6A and 6B notably does not include a second return line nor does it include the first and second isolation valves 30 and 34. The rotary valve 21 is disposed between the pump discharge line 10 and the first and second filtration lines 18, 28. As arranged, the operation of the rotary valve 21 functions to divert flow in the same manner as described for the three-way valve 14 of FIG. 1 and the pinch valve 17 of FIGS. 4A and 4B.

To effect flow through the filter housing 6 (and filter) in the direction of arrow "A" (i.e., the first mode of operation, illustrated in FIG. 6A, in which the system 1 is configured to direct flow from the vessel 2 to the first end 20 of the filter housing 6 via first filtration line 18), the rotary valve 21 is configured to direct flow from the pump discharge 10 to the first filtration line 18, and to block flow from the pump discharge to the second filtration line 24. In this configuration, the rotary valve 21 is also configured to direct flow from the second filtration line 24 to the first return line 28. Thus configured, fluid flows from the vessel 2, through the pump 4, through the rotary valve 21, then through the first filtration line 18 where it enters the first end 20 of the filter housing 6. Fluid travels through the filter housing 6 in the direction of arrow "A" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, rotary valve 21, and first return line 28.

To effect flow through the filter housing 6 (and filter) in the direction of arrow "B" (i.e., the second mode of operation, shown in FIG. 6B, in which the system 1 is configured to direct flow from the vessel 2 to the second end 26 of the filter housing 6 via second filtration line 24), the rotary valve 21 is configured to direct flow from the pump discharge 10 to the second filtration line 18, and to block flow from the pump discharge 10 to the first filtration line 18. In this configuration, the rotary valve 21 is also configured to direct flow from the first filtration line 24 to the first return line 28. Thus configured, fluid flows from the vessel 2, through the pump 4, through the rotary valve 21, then through the second filtration line 24 where it enters the second end 26 of the filter housing 6. Fluid travels through the filter housing 6 in the direction of arrow "B" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the first filtration line 18, rotary valve 21, and first return line 28.

With the embodiment of FIGS. 6A and 6B, a single pump 4 can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode. In addition, the embodiment of FIGS. 6A and 6B enables a complete volume exchange in each cycle of the rotary valve 21.

Figure 7A:
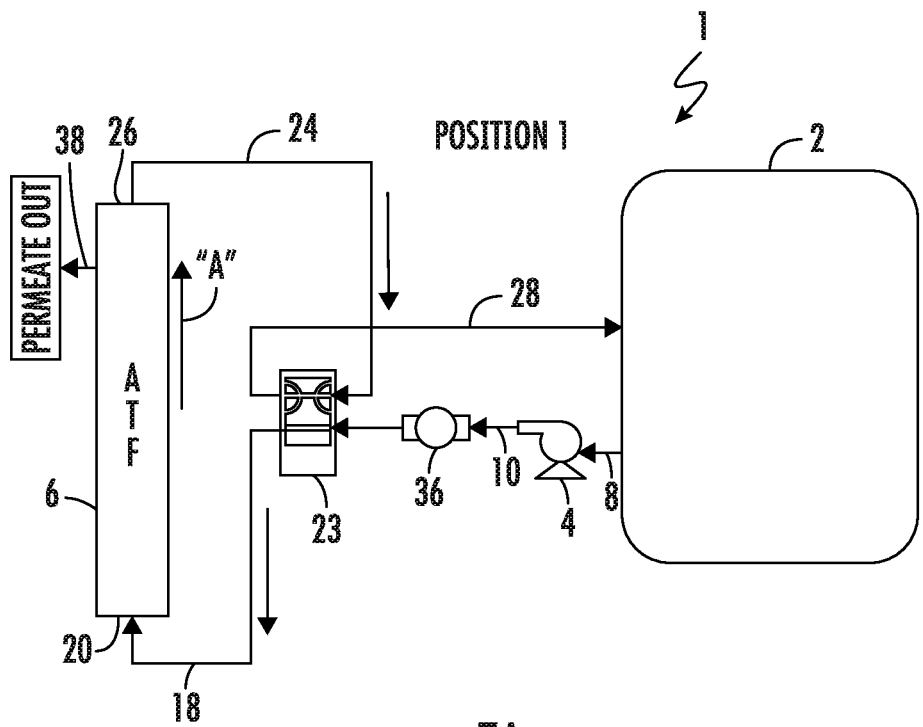
FIGS. 7A and 7B are schematic views of another example pump and filter system according to the present disclosure.
Figure 7B:
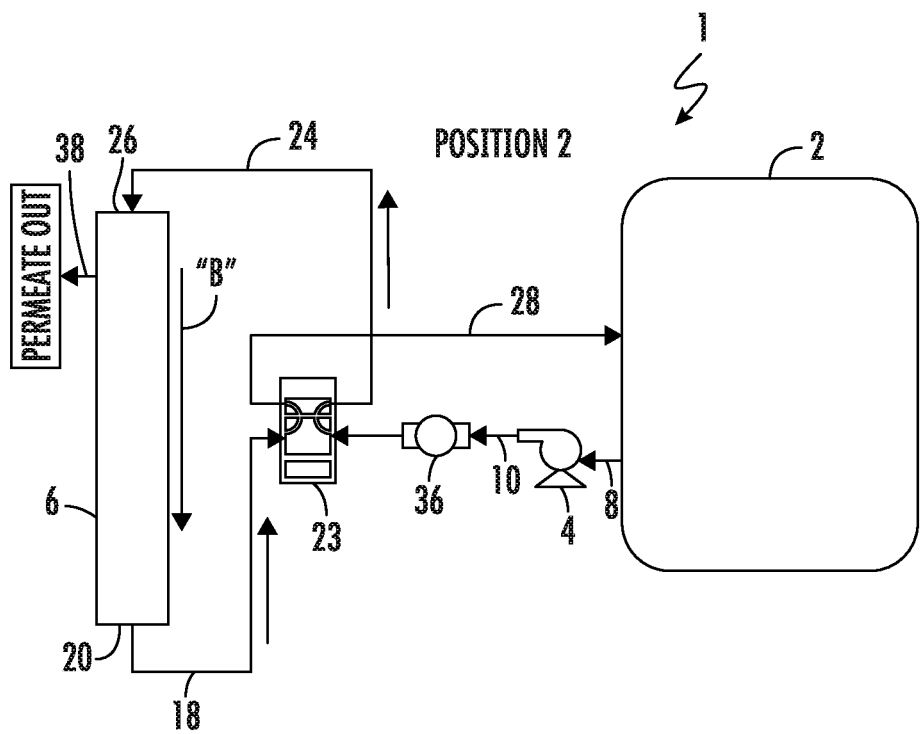

FIGS. 7A and 7B illustrate an alternative embodiment of the disclosed system 1 in which the three-way valve 14 is replaced by a shuttle valve 23. As can be seen, the system 1 of FIGS. 7A and 7B is substantially the same as the system described in relation to FIGS. 1 and 2, including vessel 2, pump 4, and filter housing 6, along with pump suction and discharge lines 8, 10, first and second filtration lines 18, 24, and first return line 28. The system 1 of FIGS. 7A and 7B notably does not include a second return line nor does it include the first and second isolation valves 30 and 34. The shuttle valve 23 is disposed between the pump discharge line 10 and the first and second filtration lines 18, 28. As arranged, the operation of the shuttle valve 23 functions to divert flow in the same manner as described for the three-way valve 14 of FIG. 1 and the pinch valve 17 of FIGS. 4A and 4B and the rotary valve 21 of FIGS. 6A and 6B.

To effect flow through the filter housing 6 (and filter) in the direction of arrow "A" (i.e., the first mode of operation, illustrated in FIG. 7A, in which the system 1 is configured to direct flow from the vessel 2 to the first end 20 of the filter housing 6 via first filtration line 18), the shuttle valve 23 is configured to direct flow from the pump discharge 10 to the first filtration line 18, and to block flow from the pump discharge to the second filtration line 24. In this configuration, the shuttle valve 23 is also configured to direct flow from the second filtration line 24 to the first return line 28. Thus configured, fluid flows from the vessel 2, through the pump 4, through the shuttle valve 23, then through the first filtration line 18 where it enters the first end 20 of the filter housing 6. Fluid travels through the filter housing 6 in the direction of arrow "A" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, shuttle valve 23, and first return line 28.

To effect flow through the filter housing 6 (and filter) in the direction of arrow "B" (i.e., the second mode of operation, shown in FIG. 7B, in which the system 1 is configured to direct flow from the vessel 2 to the second end 26 of the filter housing 6 via second filtration line 24), the shuttle valve 23 is configured to direct flow from the pump discharge 10 to the second filtration line 24 and to block flow from the pump discharge 10 to the first filtration line 18. In this configuration, the shuttle valve 23 is also configured to direct flow from the first filtration line 18 to the first return line 28. Thus configured, fluid flows from the vessel 2, through the pump 4, through the shuttle valve 23, then through the second filtration line 24 where it enters the second end 26 of the filter housing 6. Fluid travels through the filter housing 6 in the direction of arrow "B" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the first filtration line 18, shuttle valve 23, and first return line 28.

With the embodiment of FIGS. 7A and 7B, a single pump 4 can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode. The embodiment of FIGS. 7A and 7B also offers instant flow redirection (limited only by the time it takes to move the shuttle of the shuttle valve 23 between positions).

Figure 8A:
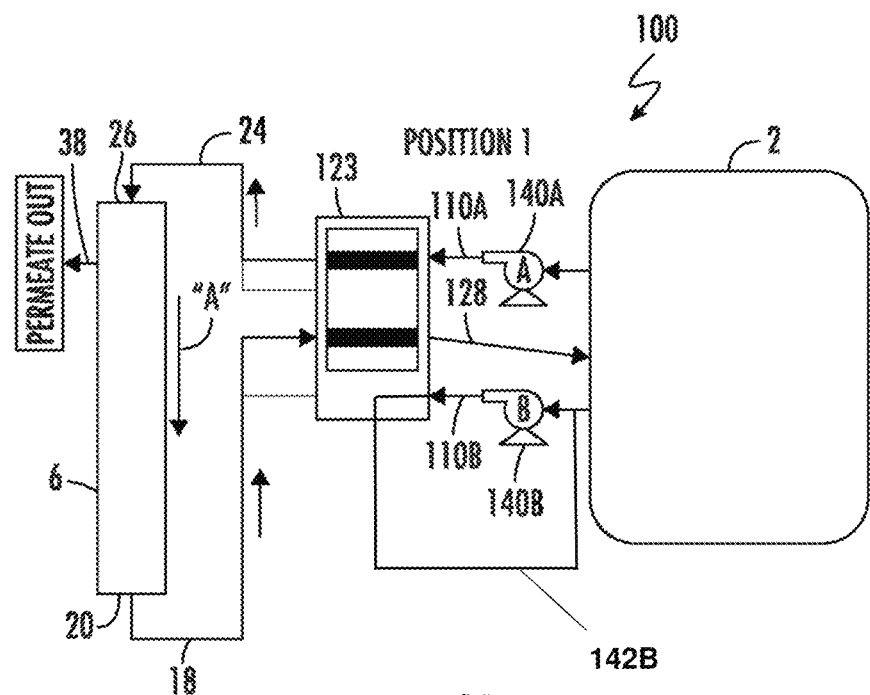
FIGS. 8A and 8B are schematic views of a further example pump and filter system according to the present disclosure.
Figure 8B:
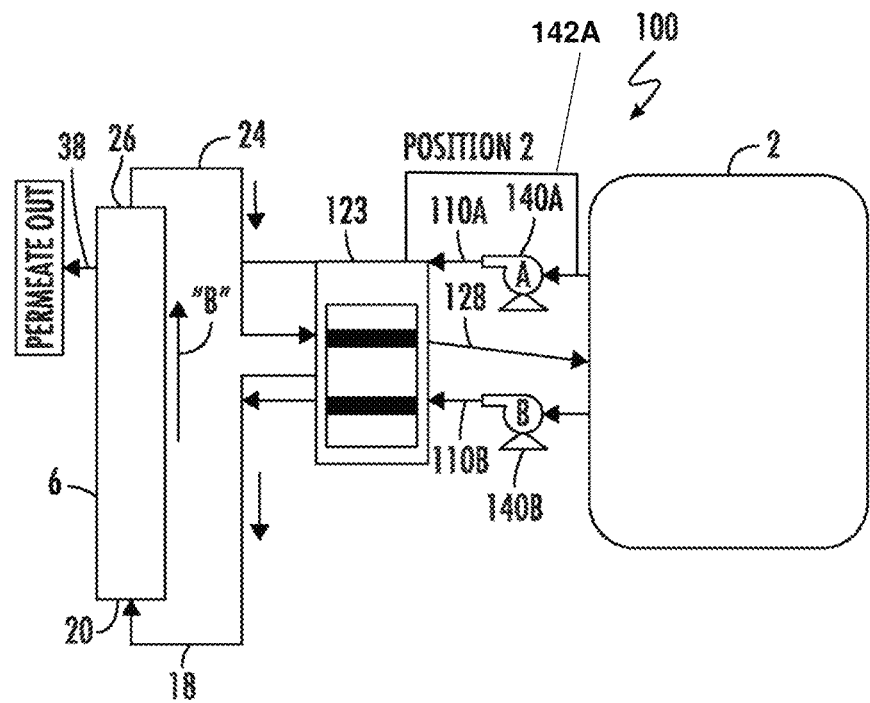

FIGS. 8A and 8B illustrate an alternative embodiment of a disclosed system 100 in which first and second pumps 140A, 140B are employed to selectively direct flow from the vessel 2 to first and second ends 20, 26 of the filter housing 6. A shuttle valve 123 is disposed between the first and second pumps 140A, 140B, and the first and second ends 20, 26 of the filter housing 6. The shuttle valve 123 is configured to selectively enable and prevent flow from the discharge of the first and second pumps 140A, 140B to the filter housing 6. As can be seen, the system 100 of FIGS. 8A and 8B is similar to system described in relation to FIGS. 1-7B, including vessel 2, filter housing 6, first and second filtration lines 18, 24 disposed between the shuttle valve 123 and the filter housing 6, and permeate line 38. The system 100 of FIGS. 8A and 8B, however, includes first and second pumps 140A, 140B each with a respective discharge line 110A, 110B coupled to the shuttle valve 123, as well as a common return line 128 coupled between the shuttle valve 123 and the vessel 2. As arranged, the operation of the shuttle valve 123 functions to selectively allow flow from the first or second pump 140A, 140B to be directed to the first or second end 20, 26 of the filter housing 6.

To effect flow through the filter housing 6 (and filter) in the direction of arrow "A" (i.e., the first mode of operation, illustrated in FIG. 8A, in which the system 100 is configured to direct flow from the vessel 2 to the second end 26 of the filter housing 6 via second filtration line 24), the shuttle valve 123 is positioned to direct flow from the discharge 110A of the first pump 140A to the second filtration line 24, and to block flow from the discharge 110B of the second pump 140B to the first filtration line 18. In this configuration, the shuttle valve 123 is positioned to direct flow from the first filtration line 18 to the return line 128. Thus configured, fluid flows from the vessel 2, through the first pump 104A, through the shuttle valve 123, then through the second filtration line 24 where it enters the second end 26 of the filter housing 6. Fluid travels through the filter housing 6 in the direction of arrow "A" and exits the first end 20 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the first filtration line 18, shuttle valve 123, and return line 128.

To effect flow through the filter housing 6 (and filter) in the direction of arrow "B" (i.e., the second mode of operation, shown in FIG. 8B, in which the system 100 is configured to direct flow from the vessel 2 to the first end 20 of the filter housing 6 via first filtration line 18), the shuttle valve 123 is positioned to direct flow from the discharge 110B of the second pump 140B to the first filtration line 18, and to block flow from the discharge 110A of the first pump 140A to the second filtration line 24. In this configuration, the shuttle valve 123 is also positioned to direct flow from the second filtration line 24 to the return line 218. Thus configured, fluid flows from the vessel 2, through the second pump 140B, through the shuttle valve 123, then through the first filtration line 18 where it enters the first end 20 of the filter housing 6. Fluid travels through the filter housing 6 in the direction of arrow "B" and exits the second end 26 of the filter housing. Fluid is filtered within the filter housing 6 and a portion of the fluid (e.g., permeate) can be evacuated from the filter housing 6 via permeate discharge line 38 using a separate pump (not shown). The remaining portion of fluid is returned to the vessel 2 via the second filtration line 24, shuttle valve 123, and return line 128.

With the embodiment of FIGS. 8A and 8B, first and second pumps 140A, 140B can be used to continuously pump cell culture from the vessel 2 (bioreactor) based on a user-defined flow rate. The cell culture flows through the filter housing 6 and filter element in a single direction (First mode "A" or Second mode "B") or selectively in two opposing directions (First Mode "A" and Second Mode "B") based on a selected operation mode. The embodiment of FIGS. 8A and 8B also offers instant flow redirection (limited only by the time it takes to move the shuttle of the shuttle valve 123 between the above-described positions).

In the embodiment of FIGS. 8A and 8B, the operation of the first and second pumps 140A, 140B can be continuous, synchronized, according to a timed schedule, and/or manually switched by a user. In a first mode of operation, the first and second pumps 140A, 140B are the same and a flow setpoint of both pumps is the same. The first and second pumps 140A, 140B are arranged for flow to occur in the same direction (i.e., drawing suction from the vessel 2 and discharging toward the filter housing 6). The first pump 140A is activated and the shuttle valve 123 is cycled so that flow from the vessel 2 is directed through the first pump 140A, through the shuttle valve 123, through the second filtration line 24, through the filter housing 6, through the first filtration line 18, then back through the shuttle valve 123 to the vessel 2 (i.e., flow path "A" shown in FIG. 8A). During this period operation, the second pump 140B is off. After a predetermined time period elapses, the first pump 140A is deactivated, the second pump 140B is activated, and the shuttle valve 123 is cycled to receive flow from the second pump so that flow from the vessel 2 is directed through the second pump 140B, through the shuttle valve 123, through the first filtration line 18, through the filter housing 6, through the second filtration line 24, then back through the shuttle valve 123 to the vessel 2 (i.e., flow path "B" shown in FIG. 8B). After a predetermined time period elapses, operation may be switched back to the first pump 140A. In this manner flow can be cycled between the first and second pumps 140A, 140B, with associated cycling of the shuttle valves 123, a plurality of times as desired.

In a second mode of operation, the first and second pumps 140A, 140B are run simultaneously and continuously, and flow through the filter housing 6 can be controlled simply by selectively cycling the shuttle valve 123 to accept discharge from the first or second pump and to direct such flow to the filter housing 6 in either direction "A" or "B" as shown in FIGS. 8A and 8B. To accommodate this second mode of operation, first and second recirculation lines 142A, 142B can be provided for each pump 140A, 140B between the shuttle valve 123 and the suction of each pump and/or the vessel so that discharge flow from the pump that is not actively pumping liquid through the filter housing 6 is recirculated back to the vessel 2 or to the pump suction. As can be seen, the shuttle valve 123 may include passages for selectively directing flow to the first or second recirculation line 142A, 142B.

Figure 9A:
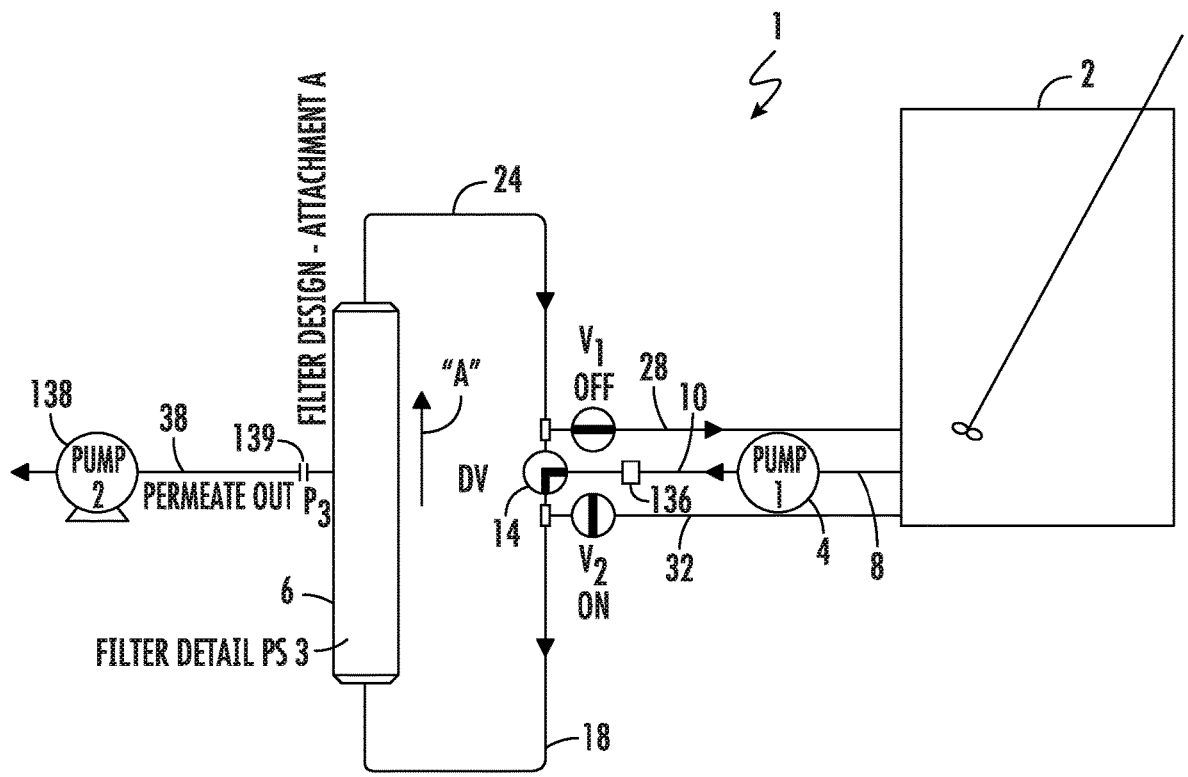
FIGS. 9A and 9B are schematic views of another example pump and filter system according to the present disclosure.
Figure 9B:
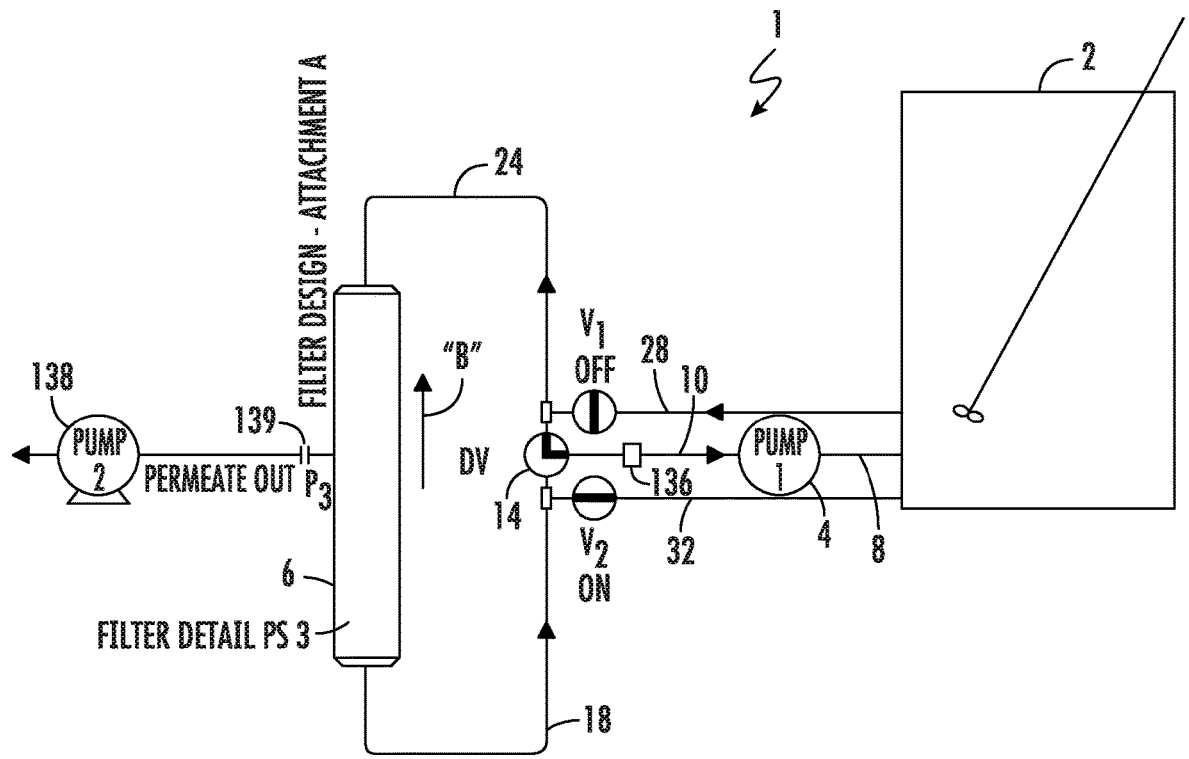

FIGS. 9A and 9B illustrate an alternative embodiment of the disclosed system 1 in which a permeate pump 138 is installed in the permeate line 38. As can be seen, the system 1 of FIGS. 9A and 9B is substantially the same as the system described in relation to FIGS. 1 and 2, including vessel 2, pump 4, and filter housing 6, along with pump suction and discharge lines 8, 10, valve 14, first and second filtration lines 18, 24, and first and second return lines 28, 32. Operation of the system 1 of FIGS. 9A and 9B is substantially the same as described in relation to FIGS. 1 and 2, including the cycling of three-way valve 14 to achieve selective flow from the vessel 2 through the filter housing 6 in first and second directions (denoted by arrows "A" an "B").

As previously mentioned, an advantage of using ATF technology is the bidirectional flow of cell couture through the hollow fiber filter (disposed in filter housing 6). The bidirectional flow of a cell culture provides a sweeping action along the inner diameter of the hollow fibers of the filter, which extends the filter's life by reducing filter fouling. Extension of filter life is important because changing filters in a continuous cell culturing process represents a risk of system contamination and a loss of cell culture product.

Thus, the system disclosed in FIGS. 9A and 9B can reduce or minimize filter fouling by employing a permeate pump 138 to reverse flow so that permeate can be directed back into the filter housing 6 to achieve a filter cleaning function. In some embodiments the permeate pump 138 is a peristaltic pump, however, it will be appreciated that the permeate pump 138 can be any type of appropriate two-directional pump. The permeate pump 138 can be controlled by the ATF(/TFF) controller algorithm embodied in controller 44 (see FIG. 15). The user may employ a filter cleaning function by activating a hollow fiber filter cleaning cycle feature. In some embodiments the cleaning cycle can include: (a) reversed flow in different flow rates, and/or (b) pulsating flow by increasing and decreasing flow rate in forward and backwords modes.

As will be understood, the permeate pump 138 normally operates in a steady pumping mode during operation of the system 1. This steady pumping mode removes permeate from the filter housing 6 and directes the permeate to a separate holding tank. When a cleaning cycle is activated, the permeate pump 138 may switch from this steady pumping mode to a filter cleaning mode for a predetermined period of time.

The filter cleaning mode can be set by a user based on trials with results formulized by validation. The cleaning step can vary between applications and can take place periodically starting at the beginning of a run. Two cleaning modes are contemplated. In a first cleaning mode the permeate pump 138 is turned off. If the permeate pump 138 is of a type that prevents flow through the permeate line 38 when the pump is turned off and subject to inlet pressure, then no additional valve is needed. If, however, the permeate pump 138 is of a typle that does not prevent flow through the permeate line 38 when the pump is turned off and subject to inlet pressure, a separate valve (not shown) can be provided to prevent permeate flow when the permeate pump 138 is turned off. In a second cleaning mode the permeate pump 138 is turned on in a reverse flow direction so that permeate flow is directed back toward the filter housing 6. In both modes, the retentate pump can be actively pumping. The retentate flow rate thus continues during the cleaning cycle, though in some embodiments it can speed up or slow down. A specific profile of the cleaning cycle with retentate pump flow rate and time of stopped or reversed permeate flow can be set and repeated for an entire run.

Once the predetermined period has elapsed, the controller 44 can switch the permeate pump 138 back to the steady pumping mode. Alternatively, the permeate pump 138 may be automatically switched to the filter cleaning mode when the fluide pressure, as sensed by pressure sensor 139 (disposed in the permeate line 38 between the permeate pump 138 and the filter housing 6) passes a predetermined value. For example, if the pressure sensed by the pressure sensor 139 is reduced to a value near a vacuum level, the permeate pump 138 may automatically be transitioned to the cleaning mode. The permeate pump 138 may remain in the cleaning mode for a predetermined time period, or until the pressure sensed by the pressure sensor 139 rises above a predetermined value.

As mentioned, when the permeate pump 138 is operating in the cleaning mode, it may reverse flow so that permeate is moved through the permeate line 38 back into the filter housing 6. Such reverse flow may occur at a constant flow rate that is the same as, greater than, or less than, the normal flowrate at which the permeate pump 138 removes permeate from the filter housing 6 under normal operating conditions. Alternatively, when the permeate pump 138 is operating in the cleaning mode, it may "pulse" flow back and forth by increasing and/or decreasing flow into and out of the filter housing.

A user interface enables a user to set the duration of stopped or reversed flow in, for example, mL/minute. In addition, the user can set the frequency of the stopped or reversed flow. Such parameters can be specific to the cell culture, size of the vessel 2, size of the filter element, and flow rate through the filter element. In some embodiments, setting the stopped or reversed permeate flow and change in retentate flow rate parameters may be determined through testing and validation.

It will be appreciated that although the embodiment of FIGS. 9A and 9B is described in relation to the pump, valve and piping/tubing arrangement of FIGS. 1 and 2, the use of a permeate pump 138 in the "cleaning mode" described above can be employed in any of the system embodiments of FIGS. 1-8B.

Figure 10:
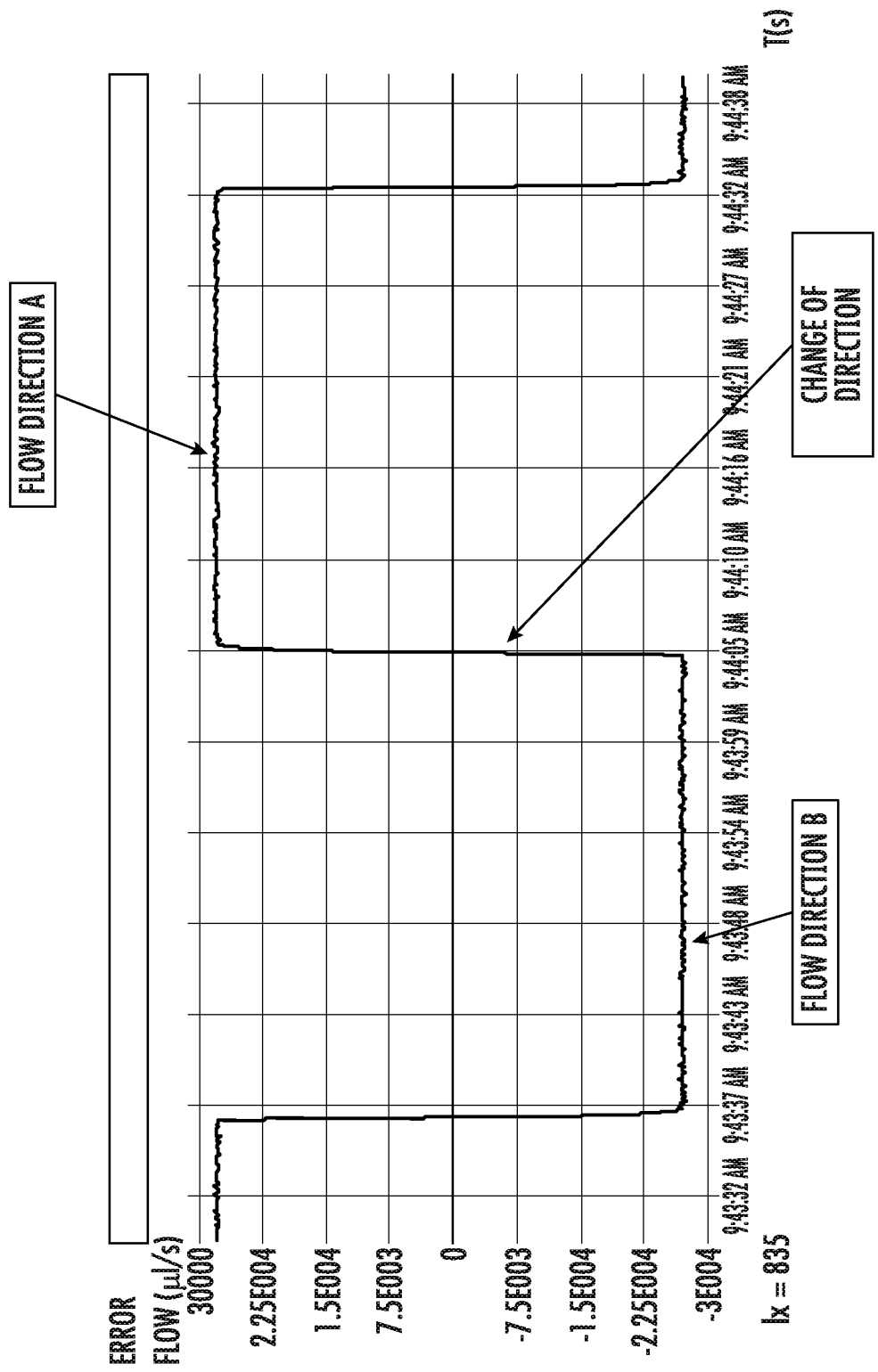
FIGS. 10-12 are graphical views of example run flow curves obtaining using one or more of the pump and filter systems of FIGS. 1-9B
Figure 11:
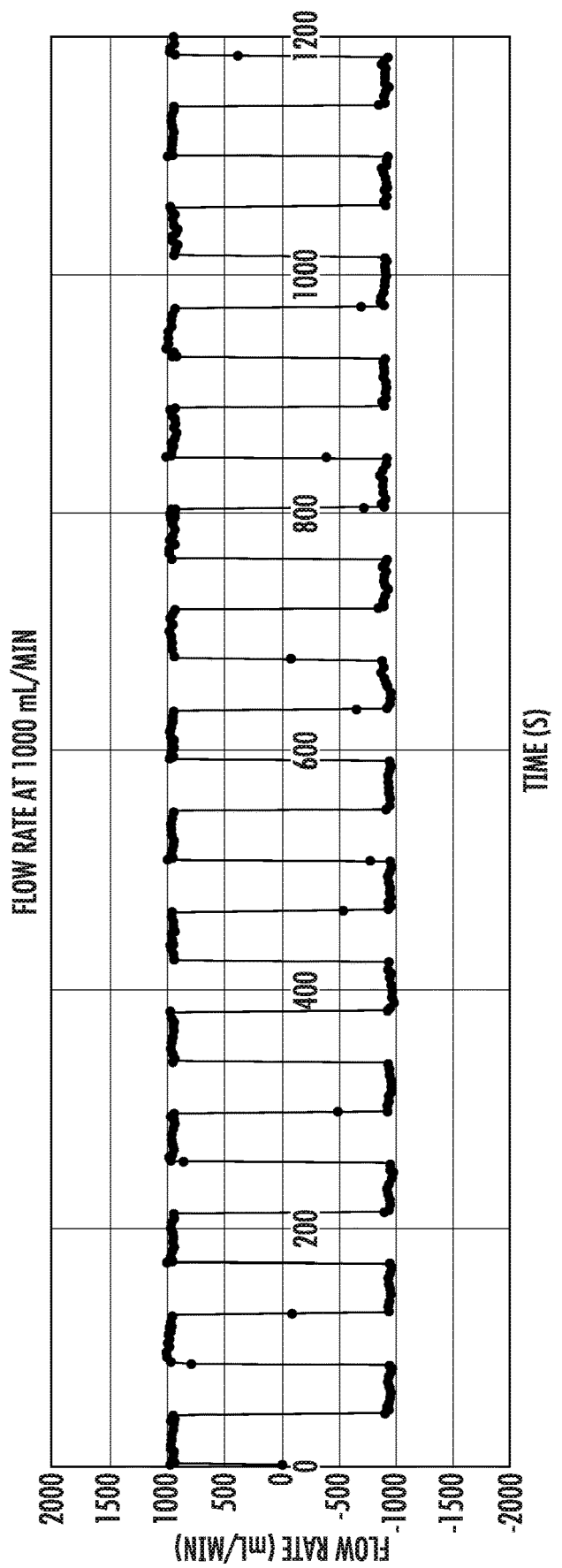
Figure 12:
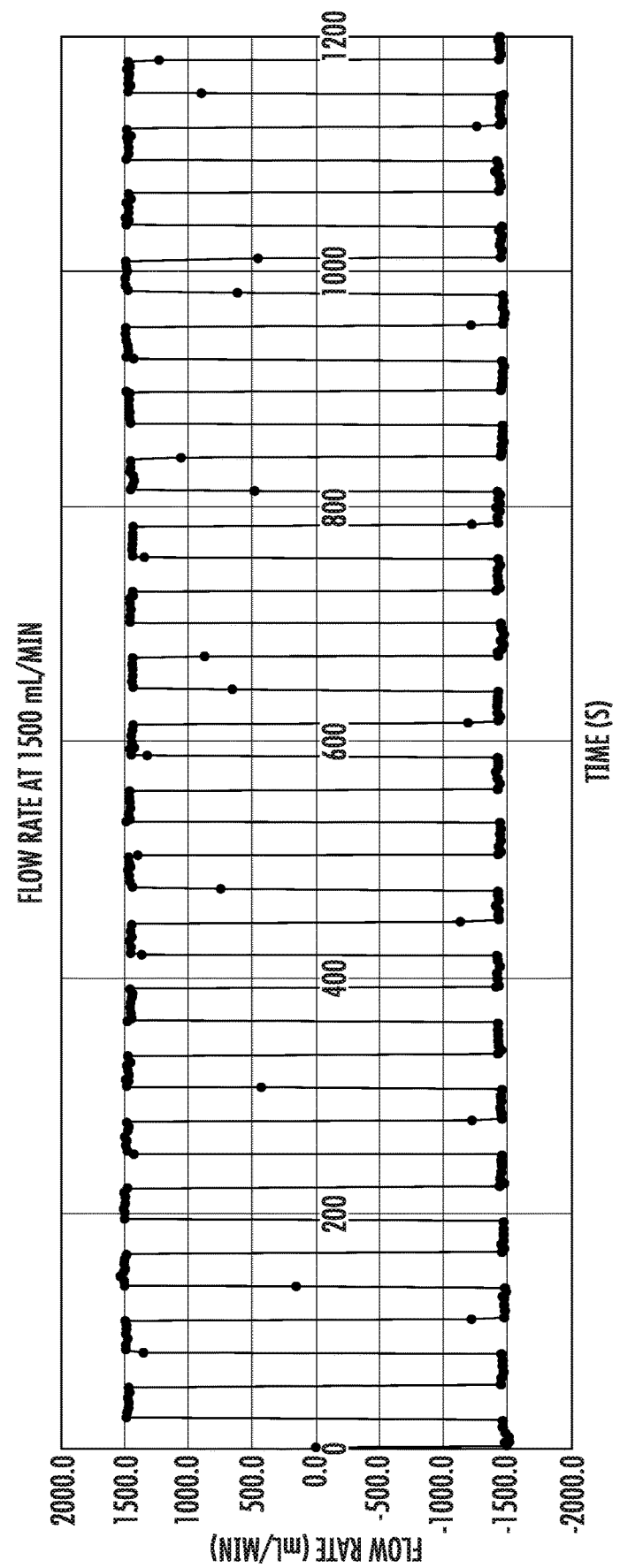

FIGS. 10-12 illustrate example flow graphs for the systems 1, 100 previously described. As can be seen in FIG. 10, "Flow Direction A" represents flow through the filter housing 6 in a first direction (e.g., in the direction of Arrow "A" in FIGS. 1-9B, while "Flow Direction B" represents flow through the filter housing 6 in a second direction (e.g., in the direction of Arrow "B" in FIGS. 1-9B. "Change of Direction" indicates the switch between flow in directions "A" and "B". As will be appreciated, this Change of Direction occurs in a nearly vertical line, illustrating the speed at which the flow change can be implemented in the disclosed systems using the described pump/valve arrangements. FIGS. 11 and 12 are example plots of flow direction changes at different system flowrates (1000 milliliters/minute for FIG. 11, and 1500 ml/min in FIG. 12).

In some embodiments cycle times may be automatically determined by a PLC algorithm based on the internal diameter of the system tubing, length of the system tubing, and pump flow rates, to assure full exchanges of, for example, the cell culture. Cycle time may consist of two directional flows, from the first and second ends 20, 26 of the filter housing 6. In non-limiting example embodiments, the cycle time can be less than 10 seconds, or longer than 30 seconds.

Figure 13:
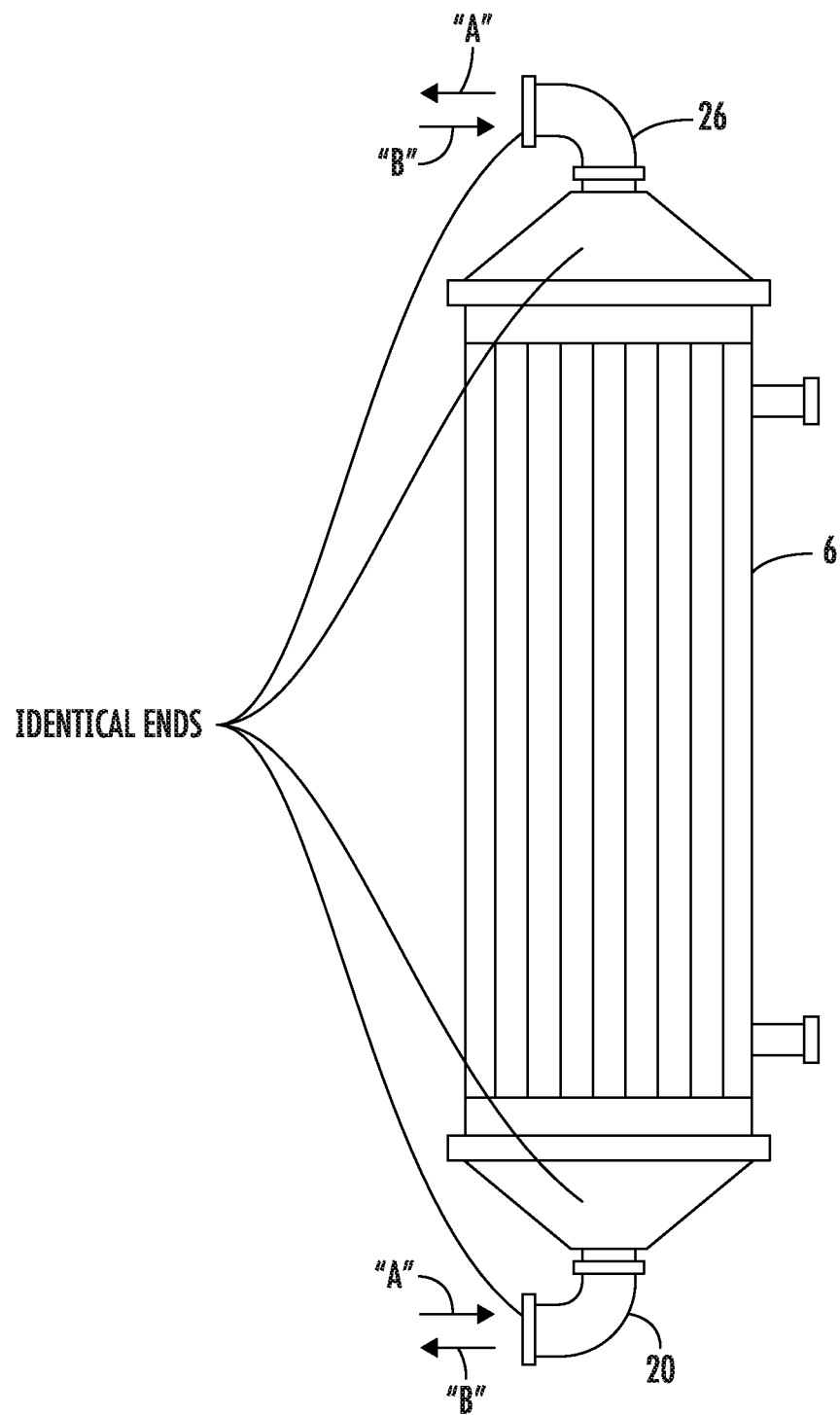
FIG. 13 is a side view of an example filter for use with the systems of FIGS. 1-9B.

FIG. 13 illustrates an example filter housing 6 includes a hollow fiber filter element. First and second ends 20, 26 of the filter housing 6 are illustrated as standard elbow connections. In the illustrated embodiment the first and second ends 20, 26 of the filter housing are functionally identical so that fluid can be passed through the filter housing equally in either direction. Fluid directions "A" and "B" are shown and relate to the first and second modes of operation described in relation to FIGS. 1-7B.

Figure 14:
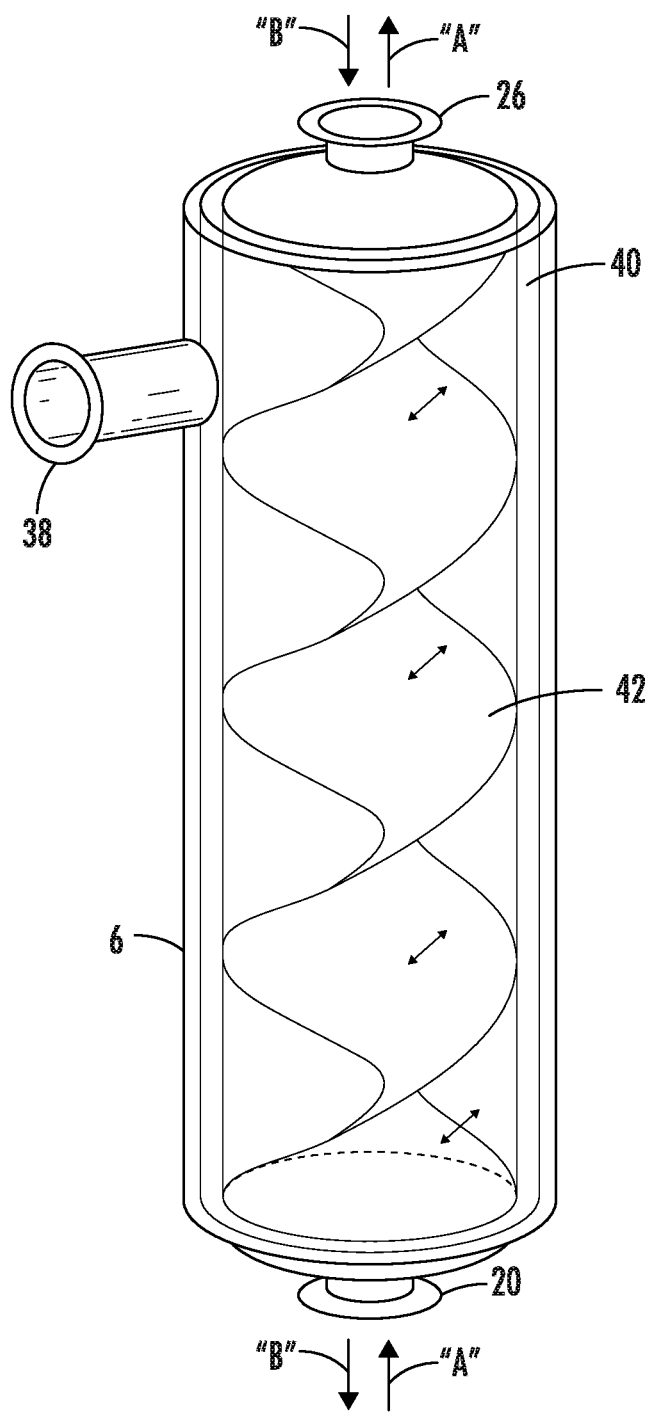
FIG. 14 is a perspective transparent view of an example filter housing and filter element for use with the system of FIGS. 1-9B.

FIG. 14 illustrates an alternative arrangement of filter housing 6 for use in the system 1 of FIGS. 1-7B. The filter housing 6 of this embodiment includes first and second ends 20, 26 similar to the filter housing described in relation to FIGS. 1-7B. A filter element 40 is disposed within the housing 6 and comprises a flat filter material sheet formed into a tube. A helix member 42 is disposed within the tube 40 and guides fluid through the housing 6, enhancing fluid contact with the filtration material wall. The helix member 42 also causes the fluid into a turbulent flow regime, with an increased Reynolds number.

A permeate discharge line 38 is disposed along the body of the housing 6 and may be coupled to a separate pump (not shown). Multiple filter housings 6 can be connected together with the use of a single retentate and a single permeate pump. The permeate discharge 38 may be disposed on the side end or in the center of the housing 6. Placing the permeate discharge 38 in the center provides the benefit of symmetry, which may be important when fluid flows in either direction "A" or "B".

Figure 15:
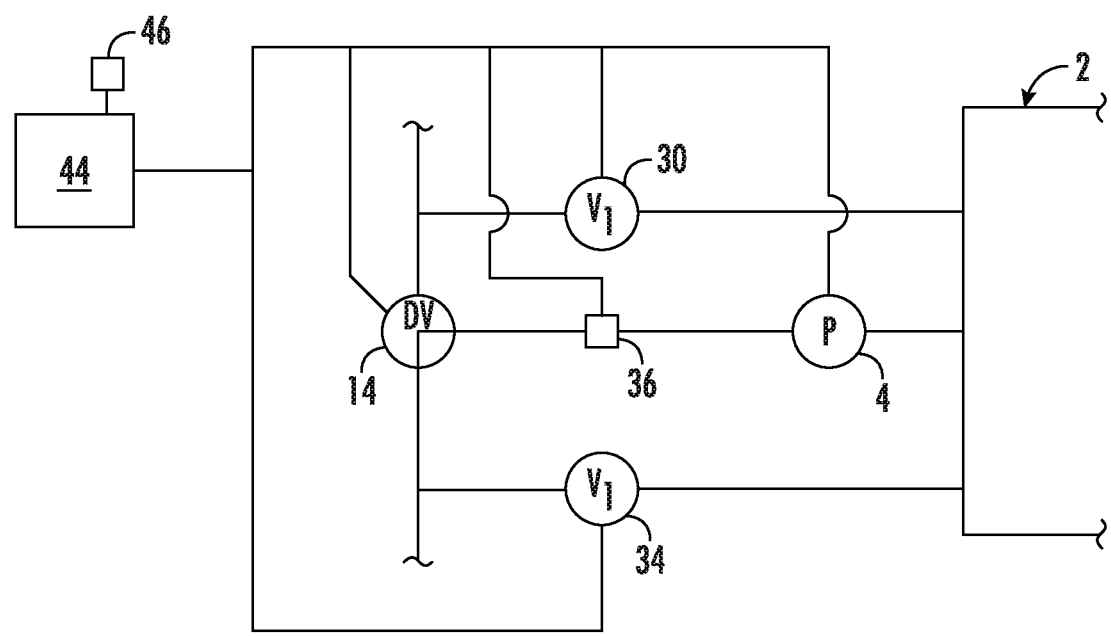
FIG. 15 is a schematic of a control system for use with the systems of FIGS. 1-7B.

Pump flow settings, redirection of flow via the three-way valve, and opening and closing of the first and second isolation valves, 30, 34, may be controlled using feedback from the flow sensor 36 disposed in the pump discharge line 10. The flow sensor 36 may confirms actual discharge flow from the pump 4, so that pump speed may be adjusted to a desired value via a controller. Referring to FIG. 15, an embodiment of electronic/computerized control operation of the system 1 disclosed in FIGS. 1-2 will be described in greater detail. It will be appreciated that this operational arrangement, employing a controller 44 as described below, can be implemented in any of the embodiments of system 1 herein (e.g., FIGS. 4A, 4B; 6A, 6B; 7A, 7B; 8A, 8B; 9A, 9B).

Actuation of the pump 4, the three-way valve 14, and the first and second isolation valves 30, 34 can be controlled by a controller 44 to allow the system 1 to operate the pump 4 and valves 14, 30, 31 in a variety of sequences and manners. The controller may include a processor or microprocessor configured to run an operating system, an application-specific integrated circuit (ASIC), a field-programmable gate array (FPGA), etc., or combinations thereof. The controller may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller can read instructions. The instructions may include code from any suitable programming language.

In some embodiments, the processor of the controller 44 may execute instructions (e.g., a subroutine) to actuate the three-way valve and the first and second isolation valves 30, 31 to reconfigure the system between the first and second operating modes. As will be appreciated, the controller 44 may also control the speed of the pump 4 adjust flow through the system 1. In some embodiments the controller 44 adjusts pump speed based on flow sensed by the flow sensor 34. A variety of set points and operating positions can be stored in controller memory 46 and executed by the processing portion of the controller 44 upon user command or automatically.

As previously mentioned, the controller 44 can include a processor and associated memory 46 for storing information regarding the pump 4, the three-way valve 14, the first and second isolation valves 30, 34, the filter element and/or other aspects of the system. The memory can include instructions executable by the processor for controlling operation of the pump 4, and the first and second isolation valves 30, 34 to thereby control flow of fluid between the vessel 2 and the filter housing 6 and filter element in any of a variety of desired manners. The controller 44 can also include a user interface for allowing a user to input information into the controller and/or operate the system 1 in a desired manner.

As will be appreciated the disclosed system 1 can be used for both tangential flow filtration (TFF) and alternating tangential flow filtration (ATF). For TFF evolutions the three-way valve 14 is maintained to direct flow in a single direction through the filter housing 6. For ATF evolutions, the three-way valve 14 is repositioned periodically to alternate flow through the filter housing (i.e., alternating between the flow direction of arrow "A" and the flow direction of arrow "B") (see FIGS. 1-9B). As will be appreciated, the disclosed system 1 can accommodate TFF and ATF operations in a single system. This is an advantage over conventional arrangements which employ separate systems for TFF and ATF.

In various embodiments, a user interface is provided where users of the disclosed systems can input and/or monitor various facets of the system and operation of associated pumps and valves. For example, the user interface may be programmed to display one or more graphical outputs of data received and analyzed by controller 44. The user interface may also display other data stored in the memory of controller 44, including type and size of filter, flow direction mode, permeate pump mode (normal, cleaning), TFF mode, ATF mode; system flow, system pressure, and system status (running, off). Further still, additional parameters that may be displayed to the user at the user interface include a flow rate and a cycle time for one or more process steps.

Further still, the user interface of certain exemplary embodiments permits the user to control starting or stopping of a control process carried out by the controller 44. In some embodiments, starting and stopping functions may be controlled via buttons provided on a touch-screen display, for example. The user interface also allows for input (entry) of specified control parameters.

As will be understood by one of ordinary skill in the art, with the disclosed systems 1 only electrical power is required for system activation, with no need for air/vacuum utilities. In addition, the disclosed systems 1 enable ATF and TFF operations in a single system. A single supply pump 4 is provided with one-directional pumping in the ATF mode. The systems 1 enable holding volume exchanges of 100% in two cycles, vs. prior systems that require six cycles to obtain less than 100% exchange. In addition, ATF filter price reduction is achieved by eliminating air/liquid hemisphere. Further, flow setpoints can be reached in 60 seconds. The systems 1 also allow synchronized flow between Levitronix (retentate) and diaphragm (permeate) pumps. The systems 1 also function without flow sensor feedback.

Figure 16:
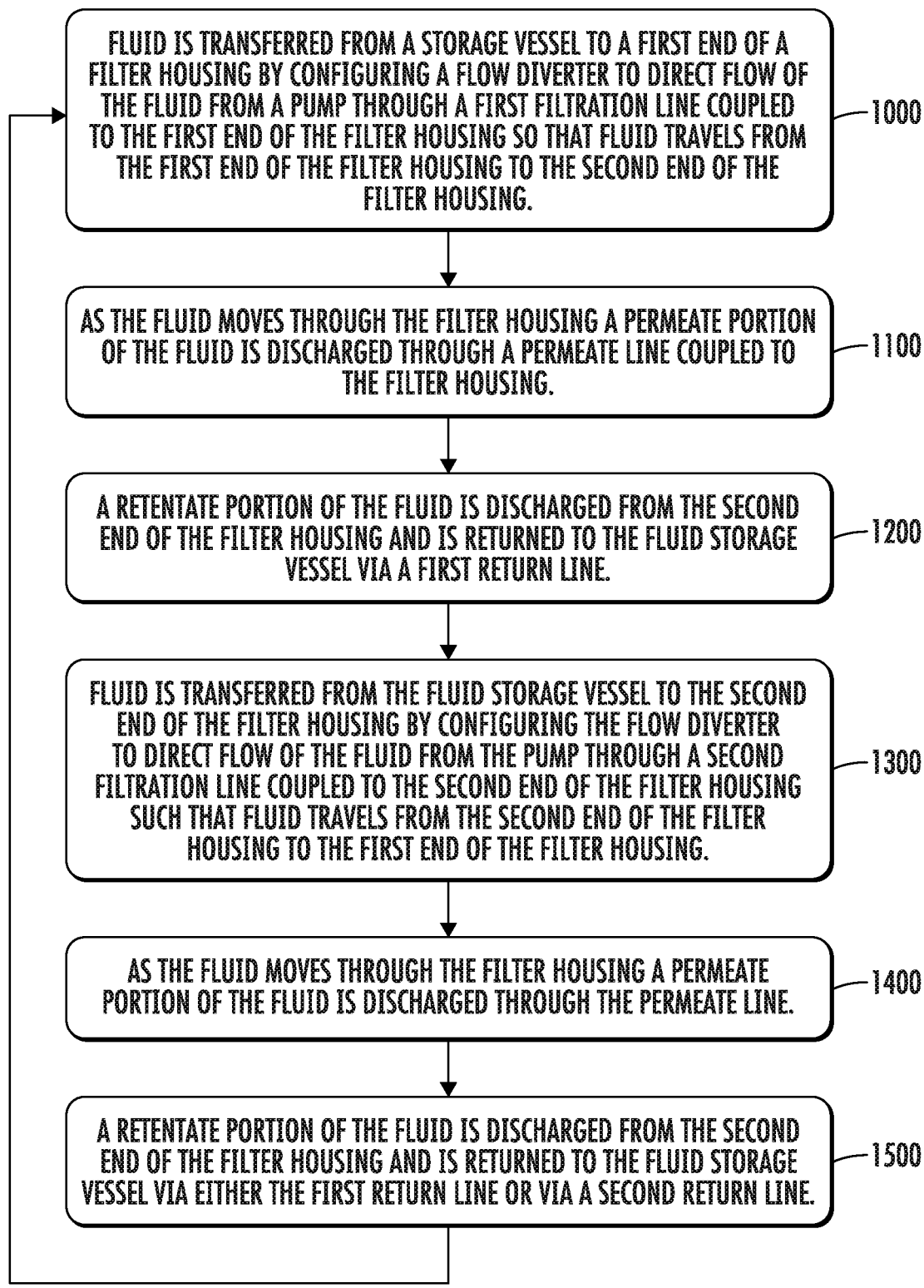
FIG. 16 is a flow diagram indicating an example process flow according to the disclosure.

An example method of operating one or more of the systems of FIGS. 1A-9B will now be described in relation to FIG. 16. At step 1000, fluid is transferred from a fluid storage vessel to a first end of a filter housing by configuring a flow diverter to direct flow of said fluid from a pump through a first filtration line coupled to the first end of the filter housing so that fluid travels from the first end of the filter housing to the second end of the filter housing. At step 1100, as the fluid moves through the filter housing a permeate portion of the fluid is discharged through a permeate line coupled to the filter housing. At step 1200, a retentate portion of the fluid is discharged from the second end of the filter housing and is returned to the fluid storage vessel via a first return line. At step 1300, fluid is transferred from the fluid storage vessel to the second end of the filter housing by configuring the flow diverter to direct flow of the fluid from the pump through a second filtration line coupled to the second end of the filter housing such that fluid travels from the second end of the filter housing to the first end of the filter housing. At step 1400, as the fluid moves through the filter housing a permeate portion of the fluid is discharged through a permeate line coupled to the filter housing. At step 1500, a retentate portion of the fluid is discharged from the second end of the filter housing and is returned to the fluid storage vessel via either the first return line or via a second return line. The process then repeats by returning to step 1000.

In some embodiments the filter element is a hollow fiber filter. In some embodiments the fluid storage vessel is a bioreactor. In some embodiments the fluid comprises cell cultures. In some embodiments the flow diverter is selected from the list consisting of a three-way valve, a pinch valve, a rotary valve, and a shuttle valve. In other embodiments the flow diverter comprises first and second flow diverter isolation valves.

As will be understood, the disclosed systems and methods provide a variety of advantages over conventional systems. For example, the disclosed systems and methods use only electrical power for ATF valve system activation (compared to conventional ATF controllers that utilize air pressure and vacuum to activate a diaphragm pump to obtain system flow.) The disclosed systems and methods allow for ATF and TFF operations in a single system. Currently each conventional method requires a separate equipment.

The electrically driven and controlled pumps of the disclosed embodiments are simpler to operate than conventional systems which are complex to operate due to the compressibility of air used to operate the diaphragm pumps employed as part of those systems. The disclosed ATF filter assembly of the disclosed embodiments eliminates the air/liquid hemisphere subassembly of conventional diaphragm pump-based systems. Such conventional ATF filter assemblies require an air/liquid subassembly, which adds to the overall filter costs in material and labor. In addition, with such conventional systems liquid flow feedback requires adjustments to the delivery of air and vacuum to the diaphragm pumps, and this indirect control of liquid flow by adjusting air pressure and vacuum requires additional time to achieve desired flowrates.

The pumps used in the disclosed systems provide unidirectional flow, compared to conventional ATF retentate pump which must pump bidirectionally. In addition, directional flow change through the filter is instantaneous, with no ramp ups or slowdowns as compared to conventional systems. Flow setpoints can thus be reached in seconds, which is an advantage over slower conventional systems.

In addition, fluctuation in flow ratio between the retentate and permeate flow can cause premature filter fouling in conventional systems. The disclosed systems and methods allow for synchronizing retentate and permeate flows and also provide methods for filter cleaning using the permeate pump in forward/reverse mode, pulse flow mode, and the like. In some embodiments changing the retentate pump flow adjusts permeate pump flow, thus extending filter functional life. As will be appreciated, in some embodiments the user sets the permeate flow at the same time as the retentate flow is activated. Permeate flow rate is determined based on the volume of the vessel 2 and perfusion flow rate (VVD). As will also be appreciated, a high permeate flow rate requires increased media addition to the vessel, which may be advantageous for cells but may be more demanding on the filter element.

Conventional systems, by contrast, require retentate and permeate pump to work independently. In some embodiments the retentate pump operates with feedback from an ultrasonic flow sensor in a closed loop operation. Flow is instantly adjusted to a setpoint. In other embodiments the system can function without flow sensor feedback using pump native flow control (i.e., by simply monitoring/controlling pump RPM and implying flow from the pump speed)

The disclosed systems and methods provide improved holdup volume exchanges with fewer cycles. In some embodiments the disclosed systems and methods facilitate a 100% holdup volume exchange in a maximum of two cycles, as compared to conventional diaphragm pump systems which require six or more cycles to achieve less than 100% holdup volume exchange.

The disclosed systems and methods have applications in perfusion of cultured animal cells as well as other varied filtration applications. Cultured animal cells can mean mammalian cells suspended in a liquid culture medium. Cultured animal cells can have a cell density of greater than about $0.1 \times 10^6$ cells/mL (e.g., greater than about $1 \times 10^6$ cells/mL, greater than about $5 \times 10^6$ cells/mL, greater than about $10 \times 10^6$ cells/mL, greater than about $15 \times 10^6$ cells/mL, greater than about $20 \times 10^6$ cells/mL, greater than about $25 \times 10^6$ cells/mL, greater than about $30 \times 10^6$ cells/mL, greater than about $35 \times 10^6$ cells/mL, greater than about $40 \times 10^6$ cells/mL, greater than about $45 \times 10^6$ cells/mL, greater than about $50 \times 10^6$ cells/mL, greater than about $55 \times 10^6$ cells/mL, greater than about $60 \times 10^6$ cells/mL, greater than about $65 \times 10^6$ cells/mL, greater than about $70 \times 10^6$ cells/mL, greater than about $75 \times 10^6$ cells/mL, greater than about $80 \times 10^6$ cells/mL, greater than about $85 \times 10^6$ cells/mL, greater than about $90 \times 10^6$ cells/mL, greater than about $95 \times 10^6$ cells/mL, or greater than $100 \times 10^6$ cells/mL).

While the present invention has been disclosed with reference to certain embodiments, numerous modifications, alterations and changes to the described embodiments are possible without departing from the spirit and scope of the invention, as defined in the appended claims. Accordingly, it is intended that the present invention not be limited to the described embodiments, but that it has the full scope defined by the language of the following claims, and equivalents thereof

What is claimed is:

1. A method of operating a fluid filtration system, the method comprising:
   transferring fluid from a fluid storage vessel, through a first pump, and to a filter housing;
   filtering the fluid within the filter housing using a filter element disposed within the filter housing, and
   removing a filtered portion of the fluid as permeate from the filter housing using a permeate pump, and
   synchronizing a permeate flowrate through the permeate pump with a flowrate through the first pump such that a change in the first pump flow-rate automatically adjusts the permeate pump flow-rate.

2. The method of claim 1, further comprising periodically performing a reverse flow operation to inject permeate back into the filter housing via the permeate pump to clean a filter element disposed in the filter housing.

3. The method of claim 2, wherein the reverse flow operation comprises reverse flow at a constant flow rate that is the same as, greater than, or less than, a normal flowrate at which the permeate pump removes permeate from the filter housing under a normal operating condition.

4. The method of claim 1, further comprising performing a pulse flow operation of the permeate flow via the permeate pump to clean a filter element disposed in the filter housing.

5. The method of claim 1, wherein the permeate flowrate is controlled via a permeate valve disposed in a permeate discharge line.

6. The method of claim 1, further comprising periodically increasing permeate flowrate through the permeate pump to clean a filter element disposed in the filter housing.

7. The method of claim 1, wherein the transferring and removing steps are performed at the same time.

8. The method of claim 1, further comprising periodically turning the permeate pump off to reduce or stop flow through the permeate pump.

9. The method of claim 1, further comprising switching the permeate pump to a filter cleaning mode when permeate pressure in a permeate discharge line passes a predetermined value.

10. The method of claim 9, wherein the permeate pump remains in the filter cleaning mode for a predetermined time, or until the permeate pressure exceeds the predetermined value.

11. A fluid filtration system, comprising:
a fluid storage vessel;
a filter housing including a filter element therein;
a first pump coupled between the fluid storage vessel and the filter housing, the first pump configured for transferring fluid from the fluid storage vessel to the filter housing;
a permeate pump coupled to the filter housing for removing a permeate from the filter housing, wherein the permeate comprises a portion of the fluid that is filtered by the filter element during operation of the system; and
a controller coupled to the first pump and the permeate pump, the controller including a processor programmed to execute instructions to control the permeate pump and the first pump to synchronize a permeate flowrate through the permeate pump with a flow rate through the first pump such that a change in the first pump flow-rate automatically adjusts the permeate pump flow-rate.

12. The system of claim 11, wherein the processor is programmed to execute instructions to control the permeate pump to periodically perform a reverse flow operation to inject permeate back into the filter housing to clean the filter element.

13. The system of claim 12, wherein the processor is programmed to execute instructions to control the permeate pump to inject permeate back into the filter housing at a constant flow rate that is the same as, greater than, or less than, a normal flowrate at which the permeate pump removes permeate from the filter housing under a normal operating condition.

14. The system of claim 11, wherein the processor is programmed to execute instructions to control the permeate pump to perform a pulse flow operation of the permeate flow to clean the filter element.

15. The system of claim 11, further comprising a valve disposed in a permeate discharge line coupled to the filter housing, wherein the controller is coupled to the valve, and wherein the processor is programmed to execute instructions to control the valve to control the permeate flowrate in the permeate discharge line.

16. The system of claim 11, wherein the processor is programmed to execute instructions to control the permeate pump to periodically increase the permeate flowrate to clean the filter element.

17. The system of claim 11, wherein the processor is programmed to execute instructions to control the first pump and the permeate pump so that the fluid is transferred from the fluid storage vessel to the filter housing and the permeate is removed from the filter housing at the same time.

18. The system of claim 11, wherein the processor is programmed to execute instructions to periodically turn the permeate pump off to reduce or stop flow through the permeate pump.

19. The system of claim 11, wherein the processor is programmed to execute instructions to switch the permeate pump to a filter cleaning mode when permeate pressure in a permeate discharge line passes a predetermined value.

20. The system of claim 19, wherein the processor is programmed to execute instructions to maintain the permeate pump in the filter cleaning mode for a predetermined time, or until the permeate pressure exceeds the predetermined value.

* * * * *